US012788600B2

(12) United States Patent
Ashby et al.

(10) Patent No.: US 12,788,600 B2
(45) Date of Patent: Nov. 10, 2026

(54) MEDICAL DEVICE DELIVERY

(71) Applicant: Covidien LP, Mansfield, MA (US)

(72) Inventors: Mark Philip Ashby, Laguna Niguel, CA (US); Danyong Zeng, Aliso Viejo, CA (US); Sydney Loan-Phuong Ngo, Riverside, CA (US)

(73) Assignee: Covidien LP, Mansfield, MA (US)

( * ) Notice: Subject to any disclaimer, the term of this patent is extended or adjusted under 35 U.S.C. 154(b) by 856 days.

(21) Appl. No.: 18/174,802

(22) Filed: Feb. 27, 2023

(65) Prior Publication Data

US 2023/0285030 A1 Sep. 14, 2023

Related U.S. Application Data

(60) Provisional application No. 63/269,157, filed on Mar. 10, 2022.

(51) Int. Cl.
*A61F 2/966* (2013.01)
*A61B 17/12* (2006.01)
*A61F 2/95* (2013.01)

(52) U.S. Cl.
CPC ...... *A61F 2/966* (2013.01); *A61B 2017/1205* (2013.01); *A61B 17/12145* (2013.01); *A61F 2002/9505* (2013.01)

(58) Field of Classification Search
CPC .... A61F 2/966; A61F 2/95; A61F 2002/9665; A61F 2/07; A61F 2002/9511; A61F 2002/9534; A61F 2/88; A61F 2/86; A61F 2/011; A61F 2002/9528; A61F 2002/9505; A61F 2/962; A61B 17/12022; A61B 17/1214; A61B 17/12145; A61B 2017/1205
See application file for complete search history.

(56) References Cited

U.S. PATENT DOCUMENTS

| | | | | |
|---|---|---|---|---|
| 10,064,747 | B2 * | 9/2018 | Berez ............... | A61B 17/12022 |
| 2005/0038496 | A1 | 2/2005 | Jones et al. | |
| 2009/0182370 | A1 | 7/2009 | Volobuyev et al. | |
| 2012/0184987 | A1 | 7/2012 | Sirota | |
| 2013/0345789 | A1 * | 12/2013 | Havel ..................... | A61F 2/962 623/1.12 |
| 2014/0277332 | A1 * | 9/2014 | Slazas ..................... | A61F 2/852 623/1.11 |
| 2016/0135984 | A1 | 5/2016 | Rudakov et al. | |
| 2016/0184117 | A1 | 6/2016 | Vad et al. | |
| 2017/0325980 | A1 | 11/2017 | Brown et al. | |

(Continued)

*Primary Examiner* — Sarah W Aleman
*Assistant Examiner* — Mikail A Mannan
(74) *Attorney, Agent, or Firm* — Fortem IP LLP

(57) ABSTRACT

Devices, systems, and methods for delivering an expandable member to a treatment site within a blood vessel are disclosed herein. According to some embodiments, a delivery system includes a core member and a coupling assembly carried by the core member. The coupling assembly may include an engagement member configured to engage an inner surface of an expandable member extending over the coupling assembly to facilitate delivery of the expandable member from an elongated shaft and/or resheathing of the expandable member into the elongated shaft. The engagement member can be movable between a radially compressed configuration and a radially expanded configuration.

20 Claims, 12 Drawing Sheets

(56) References Cited

U.S. PATENT DOCUMENTS

| | | | | |
|---|---|---|---|---|
| 2019/0125534 | A1* | 5/2019 | Arcaro .................. | A61F 2/2439 |
| 2019/0192290 | A1 | 6/2019 | Pfenniger et al. | |
| 2019/0314177 | A1* | 10/2019 | Alonso ..................... | A61F 2/90 |

* cited by examiner

MEDICAL DEVICE DELIVERY

CROSS-REFERENCE TO RELATED APPLICATION(S)

The present application claims the benefit of priority to U.S. Provisional Patent Application No. 63/269,157, titled MEDICAL DEVICE DELIVERY, filed Mar. 10, 2022, which is incorporated by reference herein in its entirety.

TECHNICAL FIELD

The present technology relates to devices, systems, and methods for delivering an expandable member, such as a medical device, to a treatment site within a blood vessel of a patient.

BACKGROUND

Walls of the vasculature, particularly arterial walls, may develop areas of pathological dilatation called aneurysms that often have thin, weak walls that are prone to rupturing. Aneurysms are generally caused by weakening of the vessel wall due to disease, injury, or a congenital abnormality. Aneurysms occur in different parts of the body, and the most common are abdominal aortic aneurysms and cerebral (e.g., brain) aneurysms in the neurovasculature. When the weakened wall of an aneurysm ruptures, it can result in death, especially if it is a cerebral aneurysm that ruptures.

Aneurysms are generally treated by excluding or at least partially isolating the weakened part of the vessel from the arterial circulation. For example, conventional aneurysm treatments include: (i) surgical clipping, where a metal clip is secured around the base of the aneurysm; (ii) packing the aneurysm with small, flexible wire coils (micro-coils); (iii) using embolic materials to “fill” an aneurysm; (iv) using detachable balloons or coils to occlude the parent vessel that supplies the aneurysm; and (v) intravascular stenting.

Intravascular stents are well known in the medical arts for the treatment of vascular stenoses or aneurysms. Stents are prostheses that expand radially or otherwise within a vessel or lumen to support the vessel from collapsing. Methods for delivering these intravascular stents are also well known.

Conventional methods of introducing a compressed stent into a vessel and positioning it within an area of stenosis or an aneurysm include percutaneously advancing a distal portion of a guiding catheter through the vascular system of a patient until the distal portion is proximate the stenosis or aneurysm. A second, inner catheter is advanced through the distal region of the guiding catheter and positioned distally of the lesion. A stent delivery system is then advanced to the distal region of the inner catheter and the distal portion of the compressed stent carried by the delivery system is positioned at adjacent a desired point of the lesion within the vessel. The compressed stent is then released and expanded so that it supports the vessel at the point of the lesion.

SUMMARY

The subject technology is illustrated, for example, according to various aspects described below. These are provided as examples and do not limit the subject technology.

In some aspects of the present technology, a device for facilitating delivery of an expandable member through an elongated shaft to a treatment site within a blood vessel is provided. The device can comprise a first end, a second end, and a central longitudinal axis extending therebetween. The device can comprise first and second engagement elements offset from one another along the central longitudinal axis. Each of the first and second engagement elements can be eccentrically shaped and defined by a perimeter comprising a first region and a second region. The device can be moveable between a radially expanded state and a radially compressed state. Each of the first regions can be closer to the central longitudinal axis in the radially compressed state than in the radially expanded state and each of the second regions can be farther from the central longitudinal axis in the compressed state than in the expanded state. The device can be configured to be positioned in the elongated shaft in the radially compressed state with the expandable member positioned between the device and an inner surface of the elongated shaft. The device can comprise a resilient material such that, when the device is in the elongated shaft in the radially compressed state, the first and second engagement elements exert an outward force against the expandable member and an inner surface of the elongated shaft and, when the device is released from the elongated shaft, the first regions move away from the central longitudinal axis and the second regions move toward the central longitudinal axis.

In some embodiments, each of the first regions and each of the second regions extends circumferentially about the central longitudinal axis. At least when the device is in the radially expanded state, the first and second engagement elements can be circumferentially offset from one another about the central longitudinal axis such that all or a portion of the first region of the first engagement element does not overlap the first region of the second engagement element. At least when the device is in the radially expanded state, each of the first regions can be diametrically opposed to its corresponding second region. An arc length and/or a radius of curvature of each of the first regions can be greater than an arc length and/or a radius of curvature, respectively, of each of the second regions at least when the device is in the radially expanded state.

A device for facilitating delivery of an expandable member through an elongated shaft to a treatment site within a blood vessel can comprise a coil having a first end portion, a second end portion, and a central longitudinal axis extending therebetween. The coil can comprise a plurality of windings including a first winding and a second winding. The coil can be moveable between a radially expanded state and a radially compressed state. At least when the coil is in the radially expanded state, a first length of the first winding can have a first radius of curvature and a second length of the first winding can have a second radius of curvature less than the first radius of curvature. The first and second lengths of the first winding can be diametrically opposed and the first length can be positioned farther from the central longitudinal axis than the second length. Additionally, a first length of the second winding can have a third radius of curvature and a second length of the second winding can have a fourth radius of curvature less than the third radius of curvature. The first and second lengths of the second winding can be diametrically opposed and the first length of the second winding can be positioned farther from the central longitudinal axis than the second length of the second winding. The coil can be configured to be positioned in the elongated shaft in the radially compressed state with the expandable member positioned between the coil and an inner surface of the elongated shaft. The coil can comprise a resilient material such that, when the coil is in the elongated shaft in the radially compressed state, the first lengths of the first and second windings exert an outward force against the expandable member and an inner surface of the elongated shaft and, when the device is released from the elongated shaft, the first lengths move away from the central longitudinal axis.

In some embodiments, the first and second windings can be circumferentially offset from one another about the central longitudinal axis such that all or a portion of the first length of the first winding does not overlap the first length of the second winding at least when the coil is in the radially expanded state. An arc length and/or a radius of curvature of each of the first lengths can be greater than an arc length and/or a radius of curvature, respectively, of each of the second lengths at least when the coil is in the radially expanded state.

A system for delivering an expandable member through an elongated shaft to a treatment site within a blood vessel in accordance with the present technology can comprise a core member configured to be slidably positioned within the elongated shaft, the core member having a proximal portion and a distal portion. The distal portion can be configured to be intravascularly positioned within a blood vessel. The system can comprise a distal member carried by the distal portion of the core member. The distal member can comprise a first end portion, a second end portion, a central longitudinal axis extending therebetween, and first and second engagement elements. Each of the first and second engagement elements can be eccentrically shaped and defined by a perimeter comprising a first region and a second region. The distal member can be moveable between a radially expanded state and a radially compressed state. Each of the first regions can be closer to the central longitudinal axis in the radially compressed state than in the radially expanded state and each of the second regions can be farther from the central longitudinal axis in the radially compressed state than in the radially expanded state. The distal member can be configured to be positioned in the elongated shaft in the radially compressed state with the expandable member positioned between the distal member and an inner surface of the elongated shaft. The distal member can comprise a resilient material such that, when the distal member is in the elongated shaft in the radially compressed state, the first and second engagement elements exert an outward force against the expandable member and an inner surface of the elongated shaft, and, when the distal member is released from the elongated shaft, the first regions move away from the central longitudinal axis.

In some embodiments, the first end portion of the distal member is fixed to the core member and the second end portion can translate and/or rotate with respect to the core member. In various embodiments, the first and second end portions of the distal member can be fixed relative to the core member. According to some embodiments, the first and second end portions of the distal member can be free to translate and/or rotate relative to the core member. A length of the distal member in the radially compressed state can be greater than a length of the distal member in the radially expanded state.

In various embodiments, the expandable member can comprise a plurality of braided filaments. In some embodiments, the expandable member comprises a laser cut stent. Additionally or alternatively, the expandable member can be configured to prevent or limit fluid flow through a sidewall of the expandable member.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

DETAILED DESCRIPTION

Figure 1A:
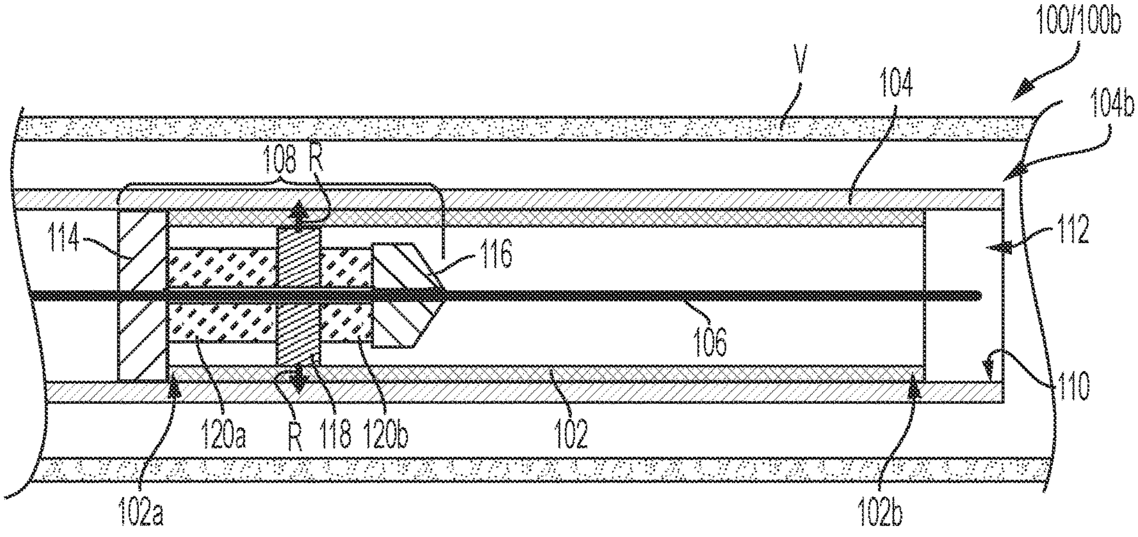
FIG. 1A is a side, cross-sectional schematic illustration of a distal end portion of a delivery system positioned within a blood vessel in accordance with the present technology.

The present technology relates to devices, systems, and methods for delivering an expandable member to a treatment site within a blood vessel. Expandable members for use with the present technology can include, for example, a braided, knit, woven, or laser-cut stent, a coil, a graft, a tubular implant, an interventional element, a medical device, etc. Some embodiments of the present technology, for example, are directed to a delivery system comprising a core member, an engagement member carried by a distal portion of the core member, and an elongated shaft. The core member and expandable member are configured to be slidably received within a lumen of the elongated shaft with the expandable member positioned between the engagement member and an inner surface of the elongated shaft. The engagement member is configured to directly engage the expandable member to facilitate delivery of the expandable member to a treatment site. In some embodiments, the engagement member is configured to apply a proximally directed force to the expandable member to draw the expandable member proximally into and/or through the lumen of the elongated shaft (for example, when resheathing the expandable member). Additionally or alternatively, the engagement member can be configured to apply a radially outward force to the expandable member to facilitate radial expansion of the expandable member once the elongated shaft has been removed.

One existing device for affecting movement of an expandable member within a shaft is a polymeric, cylindrical pad that extends along a distal portion of an elongated delivery member. The pad has an outer diameter slightly larger than an inner diameter of the compressed expandable member (e.g., larger by as little as 0.0001 in, larger by as much as 0.003 in, larger by about 0.0003 in to about 0.0015 in, etc.) such that, when the expandable member is compressed over the pad, the pad applies an outward radial force to the inner surface of the expandable member. To draw the expandable member proximally into and/or through a lumen of an elongated shaft, the core member and pad can be retracted proximally (or the elongated shaft advanced distally relative to the core member and pad) such that the pad applies a proximally directed force to the inner surface of the expandable member. In this manner, such pads can facilitate resheathing of a partially deployed expandable member into a lumen of an elongated shaft. In order to exert sufficient force on the expandable member and/or retain the expandable member in a desired position relative to the pad, the pad must be relatively long (e.g., at least 2 mm, about 6.5 mm, about 9 mm, etc.) so that a sufficient surface area of the pad contacts the expandable member. A pad with a larger contact area, however, can impart greater friction on the expandable member, thereby increasing the delivery force a user must apply to the system to deliver the expandable member. High friction applied to the expandable member can also cause distortion of pores of the expandable member. Additionally, a longer pad increases the stiffness of the delivery system, making the system more difficult to navigate through tortuous vascular. Moreover, longer pads reduce the length of the expandable member that can be deployed before resheathing is no longer possible, as longer pads need to engage a greater length of expandable member still positioned within an overlying catheter to apply sufficient force to the expandable member to enable resheathing.

Moreover, to sufficiently engage an expandable member for resheathing, existing pads are configured for use with an expandable member of a single type, configuration, and/or size. Yet, the dimensions and other properties of expandable members can vary based on a multitude of factors including a size of a blood vessel to be treated, a wire diameter of a braided expandable member, a sidewall thickness of tube stock used to form a laser-cut stent, etc. As an example, a pad can have an outer diameter based on an intended use of the pad with an elongated shaft of a specific inner diameter and an expandable member having a certain sidewall thickness. If the pad is used with the intended elongated shaft but a different expandable member having a different, smaller sidewall thickness (for example, for use in a smaller vessel), the pad may insufficiently (or not at all) contact the inner surface of the expandable member. As a result of such lack of contact, the engagement member may not exert sufficient radial force to the expandable member to be able to draw the expandable member proximally relative to the elongated shaft. Thus, conventional devices for engaging the expandable member must be manufactured in a variety of sizes to be able to deliver expandable members of a variety of sizes.

Other devices have been developed to address the limitations of the cylindrical pad and to allow a single size device to be used with a relatively broad range of expandable members within a given elongated shaft size (e.g. a 0.027 inch, a 0.021 inch, and/or a 0.017 inch inner diameter elongated shaft). Such devices include a sprocket with projections configured to extend into the pores of an expandable member and engage the expandable member along a thickness of its sidewall. However, the expandable member may remain entangled with the projections of the sprocket even after the elongated shaft is removed (e.g., projections of the sprocket may remain protruding into pores of the expandable member), and the expandable member may be prevented from foreshortening and fully radially expanding. This may be particularly likely when an expandable member is delivered to a treatment site within a tortuous vessel. When the core member carrying the sprocket is curved around a sharp bend in the vessel, the sprocket may be urged toward a side of the vessel opposite the center of curvature of the bend, thereby more forcefully pushing the projections of the sprocket into or through the pores of the expandable member. In addition, if the sprocket remains engaged with the expandable member after removal of the elongated shaft, one or more portions of the expandable member may be unintentionally drawn into the elongated shaft as the elongated shaft is advanced distally over the sprocket to retrieve the sprocket following deployment of the expandable member. Consequently, multiple manipulations of the delivery system may be required to properly deliver the expandable member.

To address the foregoing challenges associated with the expandable member remaining unintentionally engaged with the sprocket during delivery of the expandable member, at least one prior art delivery system includes a distinct release member in the form of a resilient polymeric disc positioned adjacent to the sprocket. When the expandable member is compressed over the sprocket and disc within a lumen of the elongated shaft, the disc assumes a radially compressed state with a diameter slightly smaller than its resting diameter. In the compressed state, the sprocket engages the expandable member as intended (e.g., via projections of the engagement member extending into pores of the expandable member). When the disc is released from the lumen of the elongated shaft, the disc expands to its resting diameter that is at least as large as a diameter of the sprocket. Such expansion of the disc urges the expandable member away from the sprocket and prevents unintentional reengagement of the expandable member with the sprocket. However, the addition of such a disc to a delivery system adds friction to the delivery system (relative to a system without the disc), thereby increasing the force a user must apply to the system to deliver and/or resheath the expandable member.

The engagement members disclosed herein are configured to address the various limitations of existing engagement members without requiring separate release members. Engagement members of the present technology are configured to contact an inner surface of an overlying expandable member to enable resheathing of the expandable member. However, unlike existing elongated pads, the present engagement members are resilient and movable between a radially compressed state and a radially expanded state. The present engagement members are configured to apply sufficient radial force to an overlying expandable member to enable resheathing of the expandable member without undesirable increases in delivery or resheathing force. Moreover, such resilience enables one engagement member of a single outer diameter in an expanded state to be used with a variety of types and sizes of expandable members. When an expandable member is compressed over an engagement member of the present technology (e.g., when positioned within a lumen of an elongated shaft), the engagement member may not extend into or through the pores of the expandable member, which can prevent or limit aforementioned "hang-up" of the expandable member on the engagement member. Additionally or alternatively, resilient expansion of the engagement member (e.g., upon release from the elongated shaft lumen) can facilitate radial expansion of the expandable member. Specific details of several embodiments of the technology are described below with reference to FIGS. 1A-8.

Figure 1B:
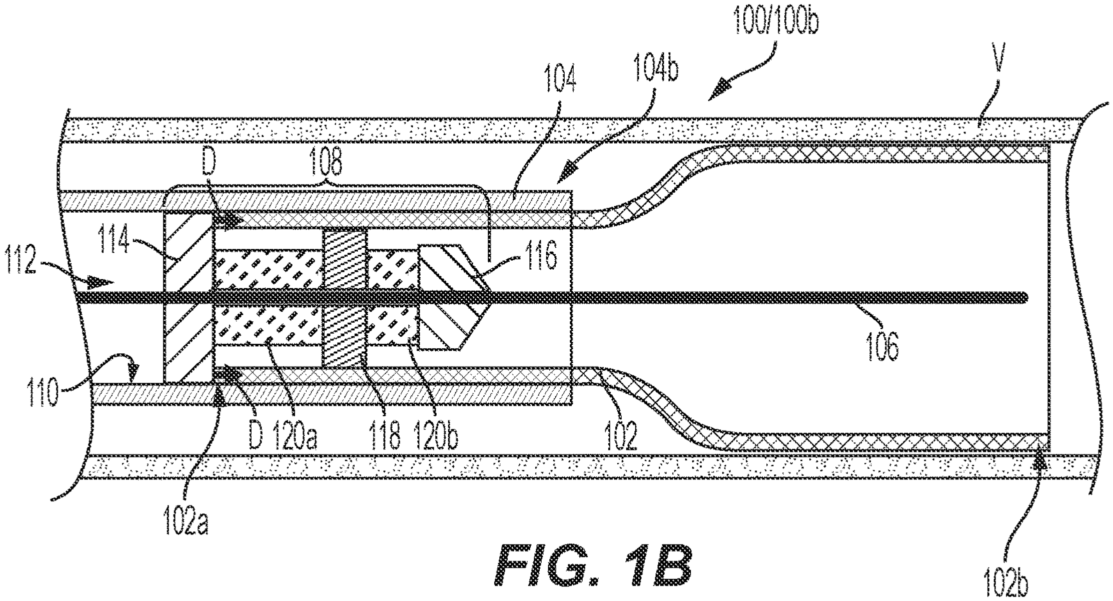
FIG. 1B illustrates partial delivery of the expandable member of FIG. 1A in accordance with the present technology.
Figure 1C:
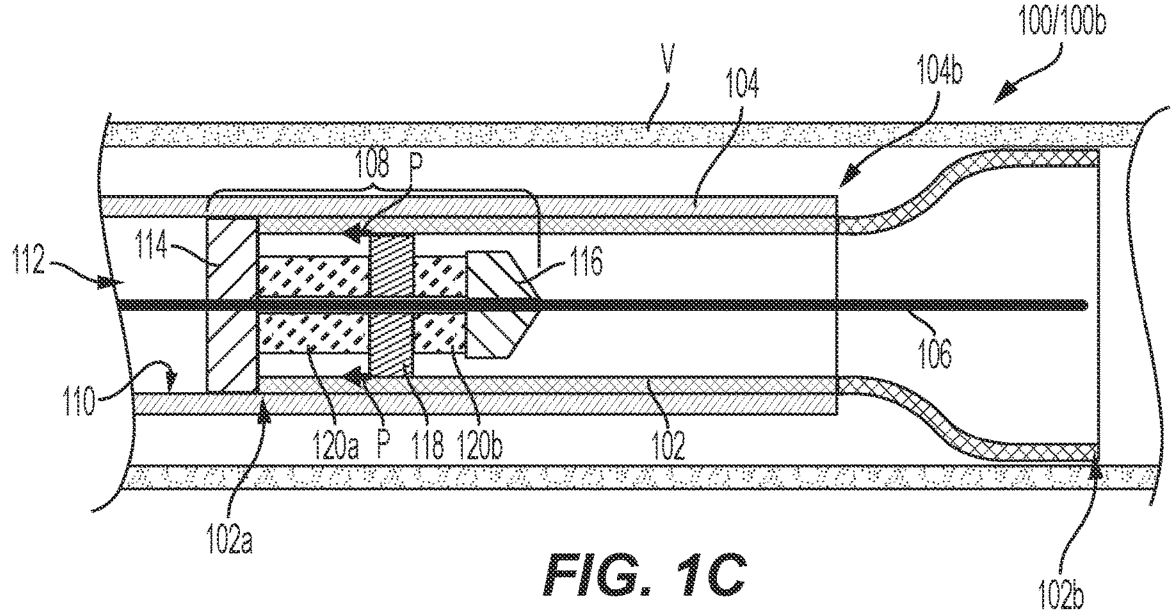
FIG. 1C illustrates partial resheathing of the expandable member of FIGS. 1A and 1B in accordance with the present technology.
Figure 1D:
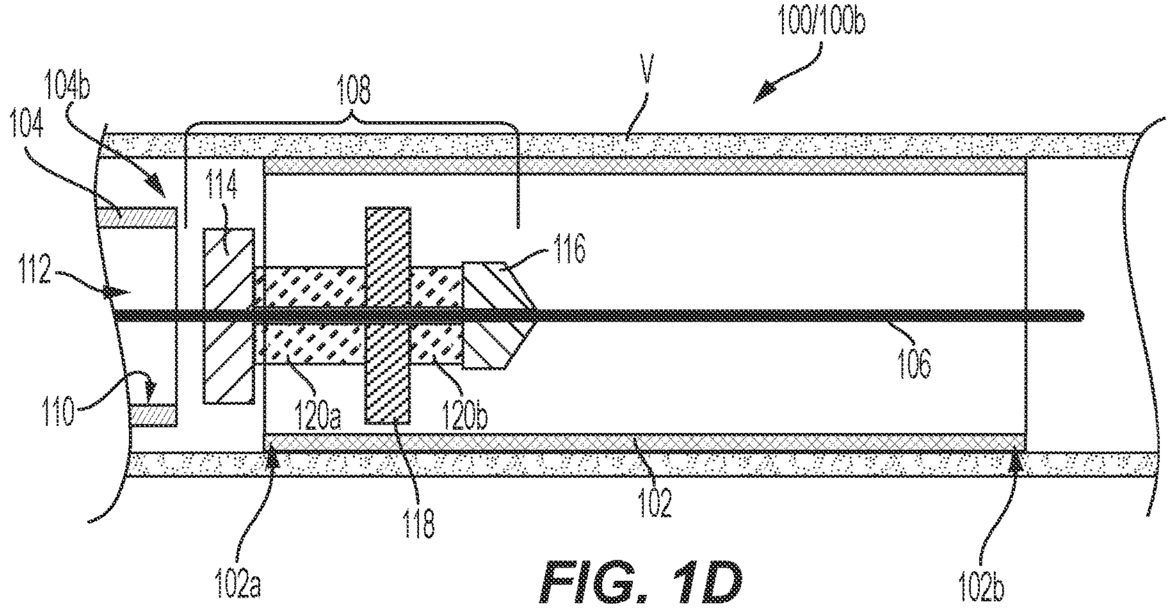
FIG. 1D illustrates complete delivery of the expandable member of FIGS. 1A-1C within the blood vessel in accordance with the present technology.

FIGS. 1A-1D are schematic illustrations of a distal portion **100*b* of a system 100 for delivering an expandable member 102 to a treatment site within a lumen of a blood vessel V in accordance with the present technology. FIG. 1A** depicts the expandable member 102 entirely contained within a lumen of an elongated shaft 104 at or near the treatment site. FIGS. 1B-1D illustrate partial delivery, partial resheathing, and complete delivery of the expandable member 102, respectively. With collective reference to FIGS. 1A-1D, the system 100 can comprise the elongated shaft 104, a core member 106 configured to be slidably positioned through a lumen of the elongated shaft 104, and a coupling assembly 108 carried by a distal portion of the core member 106. The coupling assembly 108 can comprise one or more components that are configured to engage the expandable member 102 to cause a desired movement of the expandable member 102 relative to the elongated shaft 104 and/or core member 106. As discussed in greater detail below, in some embodiments the coupling assembly 108 comprises an engagement member 118 that is configured to engage an inner surface of the expandable member 102 and move the expandable member 102 proximally relative to the elongated shaft 104 to enable resheathing of the expandable member 102.

The elongated shaft 104 can have a proximal end portion (not shown in FIGS. 1A-1D), a distal end portion 104*b* configured to be positioned at or near the treatment site, a longitudinal axis extending between the proximal end portion and the distal end portion 104*b*, and an inner surface 110 defining a lumen 112. The proximal end portion of the elongated shaft 104 may include a catheter hub. In some embodiments, the elongated shaft 104 is a catheter. For example, the elongated shaft 104 can optionally comprise any of the various lengths of the MARKSMAN™ catheter available from Medtronic Neurovascular of Irvine, California USA. In some embodiments, the elongated shaft 104 comprises a microcatheter having an inner diameter of about 0.030 inches or less (e.g., 0.027 inches, 0.021 inches, 0.017 inches, etc.), and/or an outer diameter of 3 French or less near the distal end portion 104*b*. Still, the elongated shaft 104 can comprise a microcatheter configured to access the internal carotid artery, another location within the neurovasculature distal of the internal carotid artery, or any other suitable location.

The expandable member 102, as well as any of the expandable members disclosed herein, can comprise a medical device including, but not limited to, a braided stent, a woven stent, a knit stent, a laser-cut stent, a roll-up stent, a coil, a graft, and/or another medical device. The expandable member 102 can have a therapeutic function. For example, the expandable member 102 can optionally be configured to act as a "flow diverter" device for treatment of aneurysms, such as those found in blood vessels in the brain or within the cranium, or in other locations in the body such as peripheral arteries. The expandable member 102 can optionally be similar to any of the versions or sizes of the PIPELINE™ Embolization Device marketed by Medtronic Neurovascular of Irvine, California USA. In some embodiments, the expandable member 102 can be any one of the stents described in U.S. application Ser. No. 15/892,268, filed Feb. 8, 2018, titled VASCULAR EXPANDABLE DEVICES, the entirety of which is hereby incorporated by reference herein. The expandable member 102 can be configured to transition between a radially expanded state (see FIG. 1D, for example) and a radially compressed state (see FIG. 1A, for example).

The core member 106 can generally comprise any elongated member(s) with sufficient flexibility and column strength to move the expandable member 102 through the lumen 112 of the elongated shaft 104. For example, the core member 106 can comprise a wire, tube (e.g., hypotube), braid, coil, or other suitable member(s), or a combination of wire(s), tube(s), braid(s), coil(s), etc. In some embodiments, the core member 106 can comprise a tube surrounding a wire along at least a portion of the length of the wire. The core member 106 can comprise a lubricious material, such as PTFE (polytetrafluoroethylene or TEFLON™) or other polymers, positioned on at least a portion of the tube and/or the wire. A diameter of the core member 106 may vary and/or taper along some or all of its length. The core member may include one or more fluorosafe and/or radiopaque markers (not shown) comprising a band, a deposited material, an exposed portion of the core member 106, etc. In some embodiments, the distal end portion of the core member 106 can comprise and/or carry a coil, which can facilitate navigation of the system 100 through the vasculature and/or visualization of the system 100.

The coupling assembly 108 can comprise a proximal restraint 114, a distal restraint 116, and/or an engagement member 118, all disposed on the core member 106. The coupling assembly 108 can be configured to engage the expandable member 102 to push and/or pull the expandable member 102 distally and/or proximally through the lumen 112 of the elongated shaft 104. For example, the proximal restraint 114 can be configured to apply a distally directed force D (see FIG. 1B) to the expandable member 102 to push the expandable member 102 distally and/or through the lumen 112 of the elongated shaft 104. Additionally or alternatively, the engagement member 118 can be configured to apply a proximally directed force P (see FIG. 1C) to the expandable member 102 to pull the expandable member 102 proximally and/or through the lumen 112 of the elongated shaft 104. In some embodiments, the distal restraint 116 is configured to prevent or limit distal motion of the engagement member 118 relative to the core member 106 and/or proximal restraint 114. For example, the distal restraint 116 can be fixed to the core member 106 by soldering, welding, etc. In embodiments in which the engagement member 118 and second spacer 120*b* are free to slide over the core member 106, the engagement member 118 and second spacer 120*b* can slide distally over the core member 106 until the second spacer 120*b* collides with the distal restraint 116. The engagement member 118 can in turn collide with the second spacer 120*b*, such that distal movement of the engagement member 118 relative to the core member 106 is limited by the distal restraint 116 and second spacer 120*b*.

All or a portion of the proximal restraint 114 can be positioned proximal of a proximal end portion 102*a* of the expandable member 102. The proximal restraint 114 can be configured to abut and/or contact the proximal end portion 102*a* of the expandable member 102 such that distal advancement of the proximal restraint 114 (e.g., via distal advancement of the core member 106) applies a distally directed force to the expandable member 102, thereby moving the expandable member 102 distally through the lumen 112 to expel the expandable member 102 through the opening at the distal end portion 104*b* of the elongated shaft 104. For example, FIG. 1B depicts the expandable member 102 partially expelled through the lumen 112 and partially expanded. In some embodiments, the proximal restraint 114 comprises a distal-facing surface configured to engage the proximal end portion 102*a* of the expandable member 102. For example, the proximal restraint 114 can be substantially cylindrical with a proximal-facing surface and a distal-facing surface configured to engage the proximal end portion 102*a*. The proximal restraint 114 can have an outer diameter at least as large as an outer diameter of the expandable member 102 such that a distal-facing surface of the proximal restraint 114 is configured to contact a proximal end portion 102*a* of the expandable member 102. In some embodiments, the proximal restraint 114 has an outer diameter that is smaller than a diameter of the lumen 112 of the elongated shaft 104 such that, when the proximal restraint 114 is positioned within the lumen 112, a radial gap exists between an outer edge of the proximal restraint 114 and the inner surface 110 of the elongated shaft 104. In any case, the proximal restraint 114 can be carried by the core member 106 such that distal movement of the core member 106 can cause the proximal restraint 114 to move distally and transmit distally directed push force to the expandable member 102.

The distal restraint 116 can be configured to define a maximum longitudinal spacing between the proximal restraint 114 and the engagement member 118 and/or prevent or limit distal motion of the engagement member 118 with respect to the core member 106. In various embodiments, the distal restraint 116 has a fixed position along a length of the core member 106 and/or relative to the proximal restraint 114. For example, the distal restraint 116 can be welded, soldered, and/or adhered to the core member 106. In some embodiments, the distal restraint 116 is sized to avoid or limit contact with an inner surface of the expandable member 102 during use of the system 100, as such contact can cause unintentional deformation of the expandable member 102 and/or an increase in delivery and/or resheathing forces. As shown in FIGS. 1A-1D, at least a portion of the distal restraint 116 can taper inwardly in a distal direction and/or the distal restraint 116 can have an outer diameter less than the inner diameter of the expandable member 102.

In some embodiments, proximal movement of the coupling assembly 108 (e.g., via proximal movement of the core member 106) pulls the expandable member 102 proximally through the lumen 112 of the elongated shaft 104. The engagement member 118 of the coupling assembly 108 can be configured to apply an outward radial force R to the expandable member 102 and the elongated shaft 104 when compressed within the lumen 112 of the elongated shaft 104 (see FIG. 1A). As a result, when the core member 106 and engagement member 118 are drawn proximally, the engagement member 118 can apply a proximally directed force P to the expandable member 102 (see FIG. 1C). Such proximally directed forces can cause proximal motion of the expandable member 102 and can facilitate resheathing of a partially deployed expandable member 102 into and/or through the lumen 112 of the elongated shaft 104.

When the engagement member 118 is in an unconstrained state, for example as shown in FIG. 1D, the engagement member 118 can have an outer diameter that is at least as large as the outer diameter of the proximal restraint 114 and/or the inner diameter of the expandable member 102 in the compressed state, but less than an inner diameter of the expandable member 102 in the expanded state. In some embodiments, the outer diameter of the engagement member 118 in the expanded state is at least as large as 0.012 inches, about 0.013 inches, about 0.015 inches, about 0.017 inches, about 0.021 inches, or about 0.027 inches. When the expandable member 102 is compressed over the engagement member 118 (e.g., via positioning of the expandable member 102 and engagement member 118 within a lumen of an elongated shaft 104, etc.), the engagement member 118 assumes the radially compressed state. In the radially compressed state, for example as shown in FIGS. 1A-1C, the engagement member 118 can have an outer diameter no greater than the inner diameter of the expandable member 102 in the compressed state. According to various embodiments, the outer diameter of the engagement member 118 in the compressed state can be smaller than the outer diameter of the engagement member 118 in the expanded state by at least 10%, at least 20%, at least 30%, at least 40%, at least 50%, at least 60%, at least 70%, at least 80%, or at least 90%. The compressibility of the engagement member 118 allows for expandable members 102 of various wall thicknesses to be used with the same engagement member 118. The resilience of the engagement member 118 enables the engagement member 118 to apply a radially outward force to such expandable members 102.

The engagement member 118 can have a predetermined shape in the radially expanded state and a modified shape in the radially compressed state. According to various embodiments, a maximum radial dimension of the engagement member 118 in the compressed state is less than a maximum radial dimension of the engagement member 118 in the expanded state. The engagement member 118 can be sufficiently resilient such that, when the engagement member 118 is compressed, the engagement member 118 attempts to return to its predetermined expanded shape and exerts an outward radial force on the expandable member 102. Upon release of the engagement member 118 from the radially compressed state, the engagement member 118 can radially expand to assume its predetermined expanded shape.

Because the engagement members of the present technology, including engagement member 118, can resiliently compress and expand to a greater degree than existing engagement members (e.g., pads, engagement members with projections, etc.), the engagement members of the present technology can accommodate greater variations in expandable member sidewall thickness while still exerting sufficient outward force on such expandable member to enable resheathing. Moreover, because the engagement members of the present technology resiliently expand upon release from constraint, such engagement members can be configured to urge an overlying portion of an expandable member to radially expand, thereby facilitating delivery of the expandable member.

As shown in FIGS. 1A-1D, the coupling assembly 108 can include a first spacer 120*a* positioned between the proximal restraint 114 and the engagement member 118 and/or a second spacer 120*b* positioned between the engagement member 118 and the distal restraint 116 (collectively "spacers 120"). In such configuration, the first spacer 120*a* can define a minimum relative longitudinal spacing between the proximal restraint 114 and the engagement member 118 and the second spacer 120*b* can define a minimum relative longitudinal spacing between the engagement member 118 and the distal restraint 116. The longitudinal distance between the engagement member 118 and the proximal restraint 114 can influence a length of the expandable member 102 that can be released from the elongated shaft 104 while resheathing of the expandable member 102 remains possible. Because the expandable member 102 may disengage from the engagement member 118 once expelled from the lumen 112 of the of the elongated shaft 104, resheathing of the expandable member 102 may no longer be possible once the engagement member 118 has been expelled from the lumen 112. Because the proximal restraint 114 is positioned at the proximal end of the expandable member 102, the length of the expandable member 102 that can be released while resheathing remains possible can be substantially equivalent to a total length of the expandable member 102 minus the length of the expandable member 102 positioned between the proximal restraint 114 and the engagement member 118. Additionally or alternatively, the first spacer 120*a* and/or the second spacer 120*b* can be sized to permit or limit longitudinal sliding of the engagement member 118 over the core member 106 and/or elongation of the engagement member 118. For example, if a longitudinal gap between the first spacer 120*a* and the second spacer 120*b* is greater than a longitudinal dimension of the engagement member 118, the engagement member 118 can slide over the core member 106 between the first spacer 120*a* and the second spacer 120*b*.

The first spacer 120*a* and/or the second spacer 120*b* can be configured based on a desired column strength of the system 100. For example, during resheathing of the expandable member 102 (see FIG. 1C), the second spacer 120*b* can bear proximally against the engagement member 118 to cause the engagement member 118 to pull the expandable member 102 proximally and thus, a column strength of the system 100 during resheathing can be base at least in part on a column strength of the second spacer 120*b*. In some embodiments, the first spacer 120*a* and/or the second spacer 120*b* has a tubular shape with an aperture configured to receive the core member 106 and one or more substantially planar end faces. Such planar end faces can be substantially orthogonal to a longitudinal dimension of the spacer, which can increase a contact area between the spacer and an adjacent component, thereby enhancing a column strength of the system.

In some embodiments, the first spacer 120*a* and/or the second spacer 120*b* comprises a tube and/or a coil. A spacer comprising a tube having a solid sidewall can be stiff and resist bending, which can facilitate maintaining a desired orientation of the spacer relative to adjacent components. For example, the first spacer 120*a* (or at least a proximal portion thereof) can comprise a stiff tube for facilitating even circumferential contact between the proximal restraint 114 and the proximal end portion 102*a* of the expandable member 102 to prevent or limit push forces from concentrating along and deforming certain portions of the expandable member 102. Even circumferential contact between the proximal restraint 114 and the proximal end portion 102*a* of the expandable member 102 can also prevent or limit slippage of the expandable member 102 into a radial gap between the outer edge of the proximal restraint 114 and the inner surface 110 of the overlying elongated shaft 104. In some embodiments, one or more portions of the first spacer 120*a* and/or the second spacer 120*b* (or any other spacer disclosed herein) can include flexibility-enhancing cuts (e.g., spiral cuts, periodic arcuate cuts, etc.) configured to enhance the bending flexibility of the spacer. Increased bending flexibility can facilitate navigation of the system 100 through tortuous vasculature. In some embodiments, the first spacer 120*a* and/or the second spacer 120*b* comprises a zero-pitch coil that is substantially incompressible along its length but has a desired bending flexibility.

In some embodiments, the first spacer 120*a* is separate from the proximal restraint 114 and/or the second spacer 120*b* is separate from the distal restraint 116. One or more of the spacers 120 can be secured to an adjacent restraint (e.g., the first spacer 120*a* can be secured to the proximal restraint 114, etc.). In various embodiments, one or more of the spacers 120 can be continuous with an adjacent restraint. The first spacer 120*a* and the proximal restraint 114 can comprise a single, unitary body and/or the second spacer 120*b* and the distal restraint 116 can comprise a single, unitary body.

Although the coupling assembly 108 illustrated in FIGS. 1A-1D includes one engagement member 118 and two spacers 120*a*, 120*b*, other numbers of engagement members and spacers are possible. For example, the number of engagement members and/or the number of spacers can be one, two, three, four, five, six, or more. In some embodiments, the coupling assembly 108 does not include an engagement member 118, the first spacer 120*a*, and/or the second spacer 120*b*. For example, the coupling assembly 108 can include one or more engagement member(s) 118 but no spacers.

In various embodiments, one, some, or all of the proximal restraint 114, the distal restraint 116, the engagement member 118, the first spacer 120*a*, or the second spacer 120*b* (or a portion of any such components) can be fixed to the core member 106. For example, the proximal restraint 114 and/or the distal restraint 116 can be fixed to the core member 106 to prevent or limit longitudinal movement of the coupling assembly 108 along the core member 106. A component of the coupling assembly 108 can be fixedly secured to the core member 106 via soldering, welding, adhering, clamping, crimping, etc. In some embodiments, the coupling assembly 108 or one or more components thereof can be monolithic with the core member 106. Additionally or alternatively, two or more components of the coupling assembly 108 can be fixedly secured to and/or monolithic with one another.

One, some, or all of the proximal restraint 114, the distal restraint 116, the engagement member 118, the first spacer 120*a*, or the second spacer 120*b* (or a portion of any such components) can be configured to slide, tilt, and/or rotate with respect to the core member 106. For example, one, some, or all of the proximal restraint 114, the distal restraint 116, the engagement member 118, the first spacer 120*a*, or the second spacer 120*b* can define an aperture configured to receive the core member 106 therein. The aperture can have a diameter at least as large as an outer diameter of the core member 106. In some embodiments, the aperture diameter is greater than the outer diameter of the core member 106 such that a radial gap exists between the component and the core member 106 and the component can rotate relative to the core member 106. Additionally or alternatively, the proximal and distal restraints 114, 116 can be spaced apart along a length of the core member 106 by a distance that is slightly greater than the combined length of the engagement member 118 and spacers 120 such that one or more longitudinal gaps exist between the engagement member 118 and spacers 120. In some examples, a distance between the proximal and distal restraints 114, 116 can be greater than the combined length of the engagement member 118 and spacers 120 by about 0.010 in or more, between about 0.0001 in to about 0.010 in, between about 0.0005 in to about 0.002 in, etc. Such longitudinal gap(s) can allow the engagement member 118 and spacers 120 to elongate and/or slide longitudinally along the core member 106 between the proximal and distal restraints 114, 116. In various embodiments, the engagement member 118 and/or one or more of the spacers 120 can be configured to tilt with respect to the core member 106, which can facilitate navigation of the system 100 through tortuous anatomy.

FIGS. 1A-1D illustrate use of the system 100 according to various embodiments. As shown in FIG. 1A, the distal end portion 100*b* of the system 100 can be advanced to a treatment site in the blood vessel V. During advancement of the distal end portion 100*b* to the treatment site, the coupling assembly 108 and the expandable member 102 can be contained within the lumen 112 of the elongated shaft 104 in a compressed state. In the compressed state, the engagement member 118 can apply an outwardly directed radial force to the expandable member 102, for example as shown in FIG. 1A. As previously noted, such outward radial force can be based at least in part on a resilience of the engagement member 118. During delivery of the expandable member 102, the proximal restraint 114 can engage a proximal end portion 102*a* of the expandable member 102 and apply a distally directed force to the expandable member 102. Likewise, because the engagement member 118 applies an outward force to the expandable member 102 in the compressed configuration, distal movement of the core member 106 and engagement member 118 relative to the elongated shaft 104 can cause the engagement member 118 to apply a distally directed force to the expandable member 102.

To deploy the expandable member 102, the elongated shaft 104 can be drawn proximally while proximal motion of the core member 106 is prevented or limited. Additionally or alternatively, the core member 106 can be advanced distally while distal motion of the elongated shaft 104 is prevented or limited. Either way, release of the expandable member 102 from the elongated shaft 104 allows the expandable member 102 to self-expand. In some embodiments, the expandable member 102 can be actively expanded by a separate expandable element (e.g., a balloon, a braid, a release member, etc.).

In some cases, it may be desirable to withdraw at least a portion of the expandable member 102 back into the lumen 112 of the elongated shaft 104 after the expandable member 102 is at least partially delivered. For example, a user might expand the distal portion 102*b* of the expandable member 102 before realizing that the expandable member 102 is not positioned at the intended treatment site, is not the appropriate size, etc. As shown in FIG. 1C, the expandable member 102 can be drawn proximally relative to the elongated shaft 104 such that at least a portion of the expandable member 102 is resheathed into the lumen 112. To move the expandable member 102 proximally relative to the elongated shaft 104, the elongated shaft 104 can be moved distally relative to the blood vessel V while distal motion of the core member 106 relative to the blood vessel V is prevented or limited and/or the core member 106 can be moved proximally relative to the blood vessel V while proximal motion of the elongated shaft 104 relative to the blood vessel V is prevented or limited. In some embodiments, the distal restraint 116 is fixed to the core member 106 such that proximal movement of the core member 106 relative to the blood vessel V causes proximal movement of the distal restraint 116 relative to the blood vessel V, which in turn bears proximally on the engagement member 118 (either directly or via bearing proximally on the second spacer 120*b*, which in turn bears proximally on the engagement member 118) to cause proximal movement of the engagement member 118 relative to the blood vessel V. In some embodiments, all or a portion of the engagement member 118 is fixed to the core member 106. For example, only a proximal end portion of the engagement member 118 may be fixed to the core member 106, only a distal end portion of the engagement member 118 may be fixed to the core member 106, a whole or partial length of a surface of the engagement member 118 defining an aperture of the engagement member 118 that receives the core member 106 may be fixed to the core member 106, a whole or partial circumference of a surface of the engagement member 118 defining an aperture of the engagement member 118 that receives the core member 106 may be fixed to the core member 106, etc. In some embodiments wherein the engagement member 118 is fixed to the core member 106, the coupling assembly 108 may not include a distal restraint 116. Because the engagement member 118 applies an outward force to the expandable member 102 in the compressed configuration, proximal movement of the core member 106 and engagement member 118 relative to the elongated shaft 104 can cause the engagement member 118 to apply a proximally directed force to the expandable member 102. Such a proximally directed force can move the expandable member 102 proximally relative to the elongated shaft 104 and into and/or through the lumen 112.

FIG. 1D depicts the system 100 with the expandable member 102 deployed at the treatment site and is in the expanded state. As shown in FIG. 1D, the expandable member 102 can be permitted to completely expand by positioning the distal end portion 104*b* of the elongated shaft 104 proximal of the proximal end portion 102*a* of the expandable member 302. In other words, the entire expandable member 102 can be positioned distal to and outside of the lumen 112 of the elongated shaft 104. Once the engagement member 118 is positioned distal to and outside of the lumen 112, the engagement member 118 can radially expand and/or assume a predetermined shape. As shown in FIG. 1D, an outer diameter of the engagement member 118 in the expanded state can be at least as large as an outer diameter of the proximal restraint 114, but may be smaller than an inner diameter of the expandable member 102 in its expanded state.

As shown in FIG. 1D, with the engagement member 118 released from the lumen 112 and both of the engagement member 118 and the overlying portion of the expandable member 102 permitted to expand, the engagement member 118 may no longer engage an inner surface of the expandable member 102 and thus no longer apply a proximally directed resheathing force to the expandable member 102. As a result, it may be advantageous for the engagement member 118 to be positioned just distal to the proximal restraint 114 (e.g., spaced apart by no more than 6 mm, spaced apart by no more than 3 mm, spaced apart by no more than 2 mm, etc.) such that a greater length of the expandable member 102 can be delivered before the engagement member 118 is released from the lumen 112 and resheathing of the expandable member 102 is no longer possible. In some embodiments, the engagement member 118 can be positioned relative to the proximal restraint 114 such that resheathing is possible after at least 60% of the expandable member 102 has been deployed, at least 75% of the expandable member 102 has been deployed, at least 80% of the expandable member 102 has been deployed, at least 85% of the expandable member 102 has been deployed, at least 90% of the expandable member 102 has been deployed, or at least 95% of the expandable member 102 has been deployed.

Figure 2A:
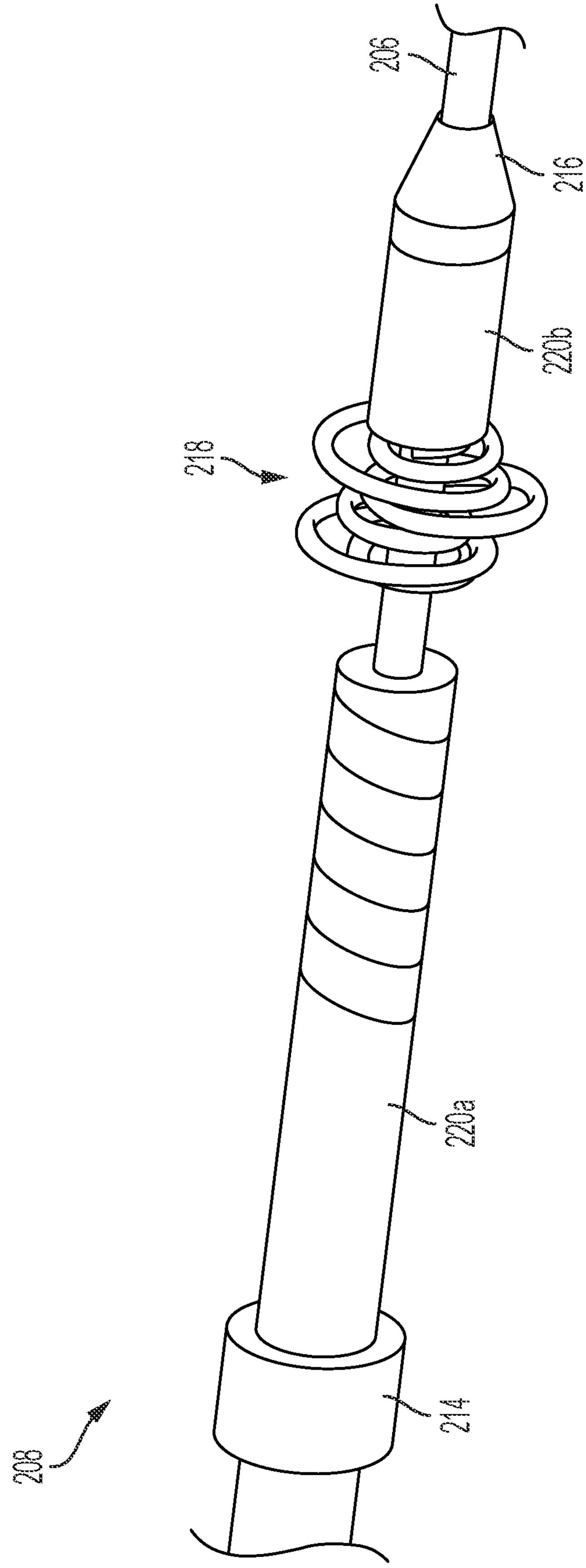
FIG. 2A is a perspective view of a coupling assembly in accordance with the present technology.
Figure 2B:
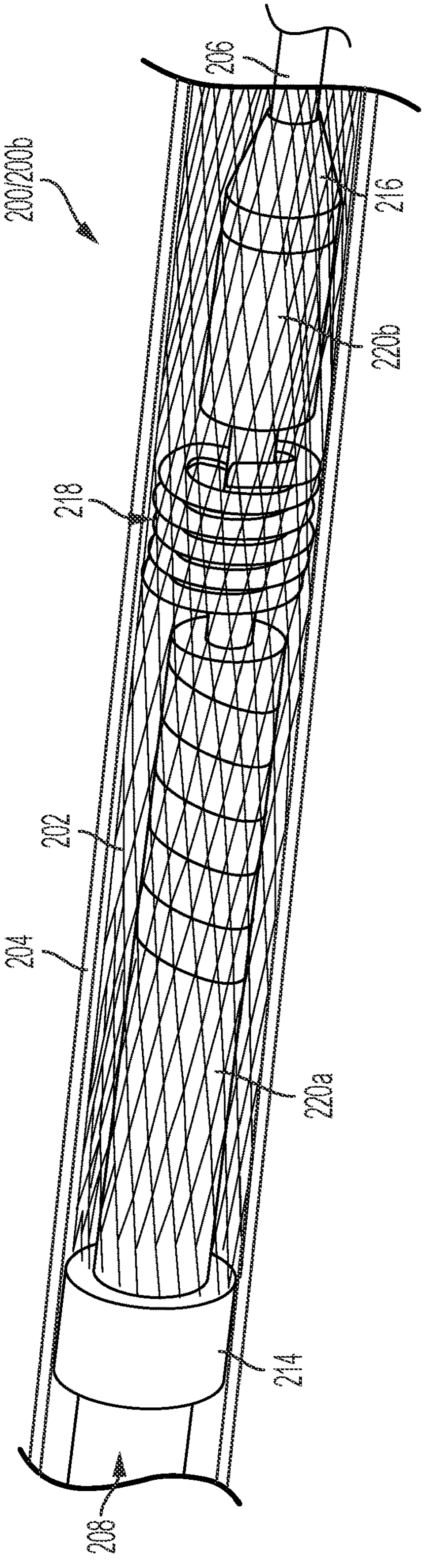
FIG. 2B is a perspective view of the coupling assembly of FIG. 2A and an expandable member in a compressed state within a lumen of an elongated shaft in accordance with the present technology.

FIGS. 2A and 2B show an example of a distal portion 200*b* of a system 200 for delivering an expandable member 202 (shown in FIG. 2B only) to a treatment site within a lumen of a blood vessel in accordance with the present technology. FIG. 2A shows the system 200 in a resting, expanded configuration without the expandable member 202 and elongated shaft 204, and FIG. 2B shows the system 200 with the expandable member 202 loaded in an elongated shaft 204.

The features of the system 200 can be generally similar to the features of the system 100 of FIGS. 1A-1D. Accordingly, like numbers (e.g., proximal restraint 214 versus proximal restraint 114) are used to identify similar or identical components in FIGS. 1A-1D. Additionally, any of the features of the system 200 can be combined with each other and/or with the features of the system 100 of FIGS. 1A-1D. For example, the system 200 can comprise an elongated shaft 204 (FIG. 2B only), a core member 206 configured to be slidably positioned through a lumen of the elongated shaft

204, and a coupling assembly 208 carried by a distal portion of the core member 206 and configured to engage the expandable member 202 during delivery and deployment. As described with reference to FIGS. 1A-1D, the coupling assembly 208 can comprise a proximal restraint 214, a distal restraint 216, and the engagement member 218 positioned between the proximal and distal restraints 214, 216. In some embodiments, the coupling assembly 208 comprises a first spacer 220*a* positioned between the proximal restraint 214 and the engagement member 218 and/or a second spacer 220*b* positioned between the engagement member 218 and the distal restraint 216 (collectively "spacers 220"). As shown in FIGS. 2A and 2B and as described previously with respect to the spacers 120 of FIGS. 1A-1D, the first spacer 220*a* can comprise flexibility-enhancing cuts.

Figure 2C:
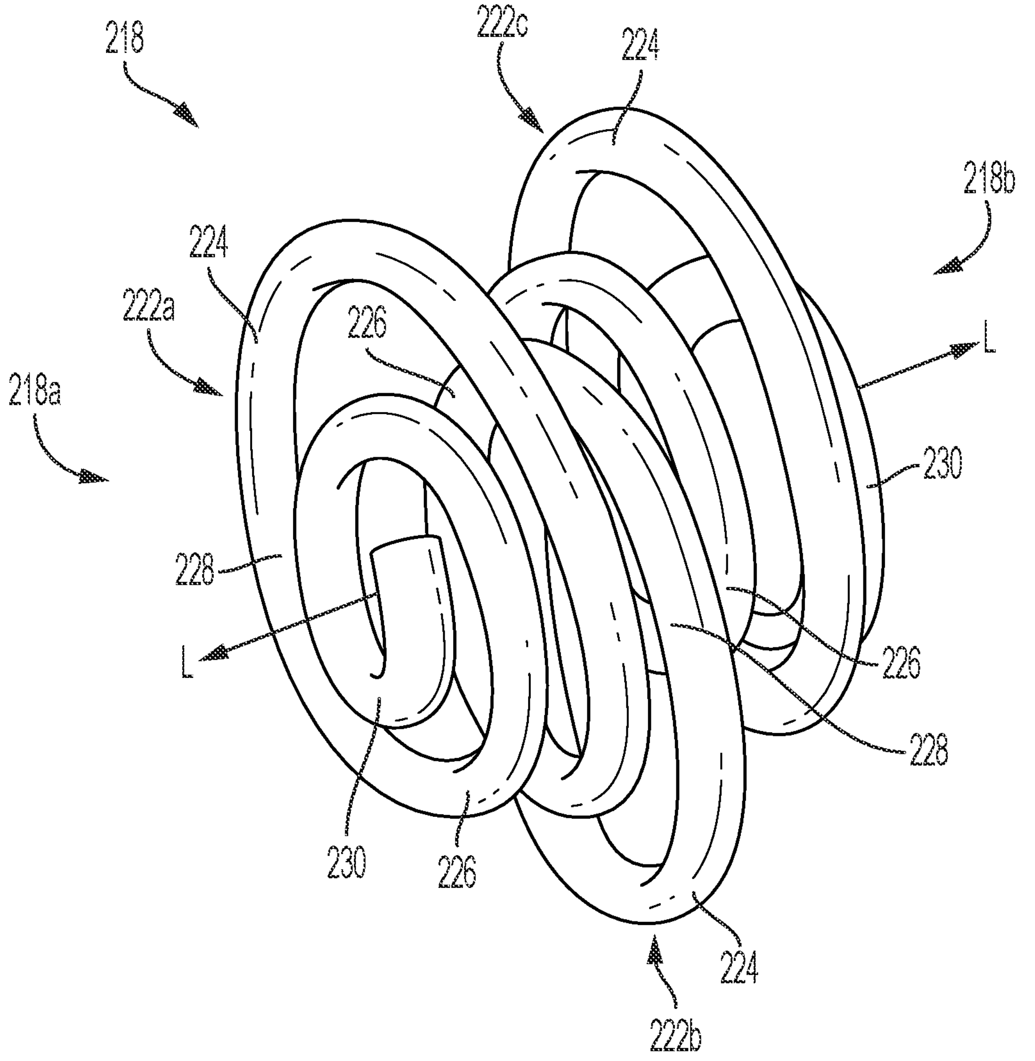
FIGS. 2C and 2D are isolated perspective and end views, respectively, of the engagement member of FIG. 2A.
Figure 2D:
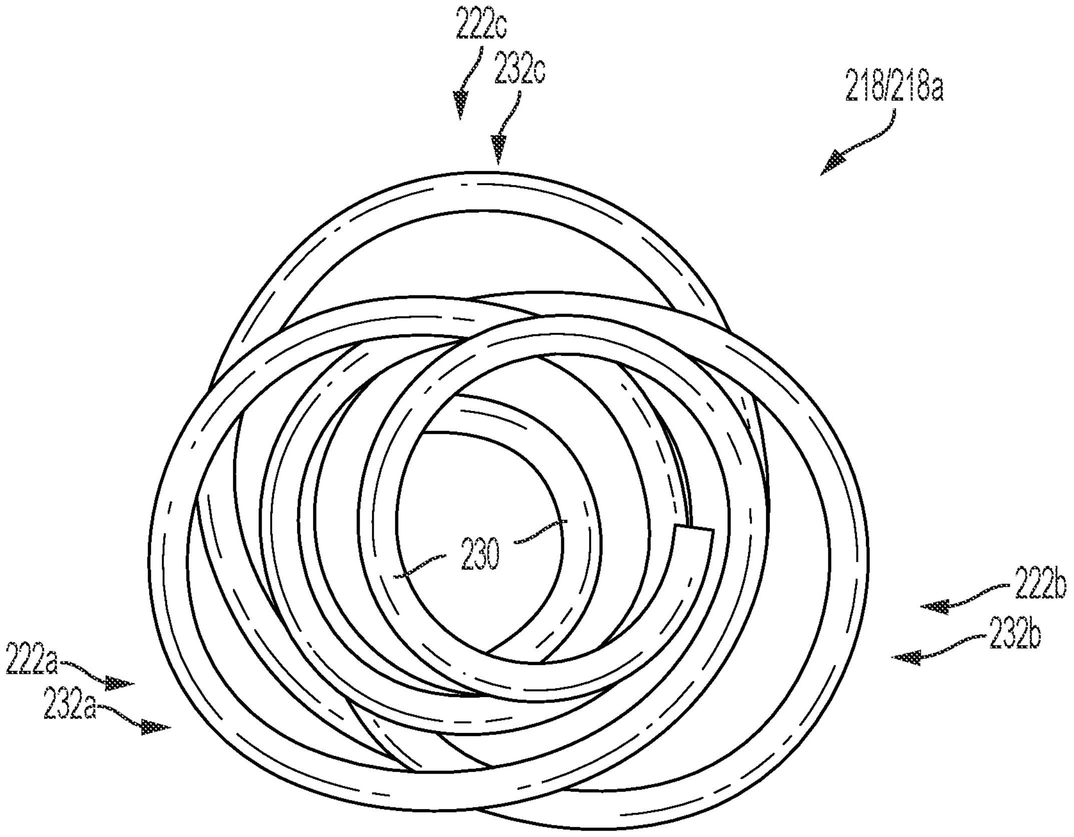

FIGS. 2C and 2D are end and perspective views, respectively, of the engagement member 218 of FIGS. 2A and 2B in an expanded state and isolated from the expandable member 202, the elongated shaft 204, and the coupling assembly 208. Referring to FIGS. 2A-2D, the engagement member 218 can comprise a first end portion 218*a*, a second end portion 218*b*, and a central longitudinal axis L extending therebetween. The engagement member 218 can have a relaxed, unconstrained state (FIGS. 2A, 2C and 2D) and a compressed state (FIG. 2B). In some embodiments, the engagement member 218 is resilient such that the engagement member 218 is configured to transition between the unconstrained state and the compressed state. The resilience of any of the engagement members disclosed herein can be based at least in part on a shape and/or a material property of the engagement member.

As depicted in FIGS. 2A-2D, in some embodiments the engagement member 218 comprises a coil. In other embodiments, the engagement member 218 comprises one or more of a tubular element with radially-extending protrusions, a polymeric disc with radially-extending petals, or another type of resilient structure with one or more radially-extending protrusions. In some embodiments, the engagement member 218 can comprise a first engagement element 222*a*, a second engagement element 222*b*, and a third engagement element 222*c* (collectively "engagement elements 222"). According to various embodiments, each of the engagement elements 222 can be configured to contact less than a full circumference of an expandable member as the expandable member is initially compressed over the engagement member 218. Because radial compression is not initially applied to the entire circumference of each of the engagement members 222, the engagement members 222 able to shift rather than deform under the compression and can maintain a desired elasticity and resilience. Each of the engagement elements 222 can be longitudinally offset from adjacent engagement elements 222 along the central longitudinal axis L of the engagement member 218. Such longitudinal spacing of the engagement elements 222 can enable the use of multiple engagement elements 222 that, in combination, are configured to engage an entire circumference of an overlying expandable member while maintaining the ability of the engagement elements 222 to shift rather than deform. Additionally or alternatively, each of the engagement elements 222 can be circumferentially offset from adjacent engagement elements 222 about the central longitudinal axis L at least when the engagement member 218 is in the expanded state. Each engagement element 222 can be angularly spaced apart from one or more longitudinally adjacent engagement elements 222 about a circumference of the engagement member 218 by about 180 degrees, about 150 degrees, about 120 degrees, about 90 degrees, about 60 degrees, about 30 degrees, between about 30 degrees and about 180 degrees, between about 60 degrees and about 150 degrees, or between about 90 degrees and about 120 degrees.

In various embodiments, one or more of the engagement elements 222 can be eccentrically shaped such that at least one portion of the engagement element is farther from the longitudinal axis L than another portion. The one or more engagement elements 222 can be defined by a perimeter comprising at least a first region 224 and a second region 226 diametrically opposed to the first region 224. Each of the first regions 224 and each of the second regions 226 can extend in a circumferential direction about the central longitudinal axis L of the engagement member 218. At least when the engagement member 218 is in an unconstrained, expanded state, the first region 224 can have a greater radius of curvature and/or arc length than the second region 226. According to various embodiments, the perimeter of each engagement element 222 can comprise a third region 228 extending radially between the first region 224 and the second region 226 at least when the engagement member 218 is in the expanded state. When the engagement member 218 is in the expanded state, for example as shown in FIGS. 2A, 2C and 2D, the first region 224 of each engagement element 222 can be further from the central longitudinal axis L than when the engagement member 218 is in the compressed state, for example as shown in FIG. 2B. Moreover, when the engagement member 218 is in the expanded state, the second region 226 of each engagement element 222 can be closer to the central longitudinal axis L than when the engagement member 218 is in the compressed state. Thus, when the expandable member 202 is radially compressed over the engagement member 218, the expandable member 202 can, at least initially, contact only a portion of each engagement element 222, which can cause the engagement elements 222 to shift relative to one another and the central longitudinal axis L. In some embodiments, one or more portions of the engagement member 218 can rotate and/or deform in response to compression by the expandable member 202. In any case, an outer diameter of the engagement member 218 in the compressed state (see FIG. 2B, for example) can be less than or equal to an inner diameter of the expandable member 202 and/or an outer diameter of the proximal restraint 214. When the engagement member 218 is released from the compressed state and assumes the expanded state, the first regions 224 can move away from the central longitudinal axis and the second regions 226 can move towards the central longitudinal axis L and the outer diameter of the engagement member 218 can increase.

As shown in FIGS. 2A-2D, in some embodiments the first end portion 218*a* and/or the second end portion 218*b* of the engagement member 218 comprises one or more centering elements 230 configured to center the engagement member 218 over the core member 206 and/or anchor the engagement member 218 to the core member 206. The one or more centering elements 230 can have a diameter that is slightly larger than an outer diameter of the core member 206. Thus, when the engagement member 218 is positioned on the core member 206, the centering element 230 can prevent or limit radial movement of the central longitudinal axis L of the engagement member 218 away from a central longitudinal axis of the core member 206.

Figure 2E:
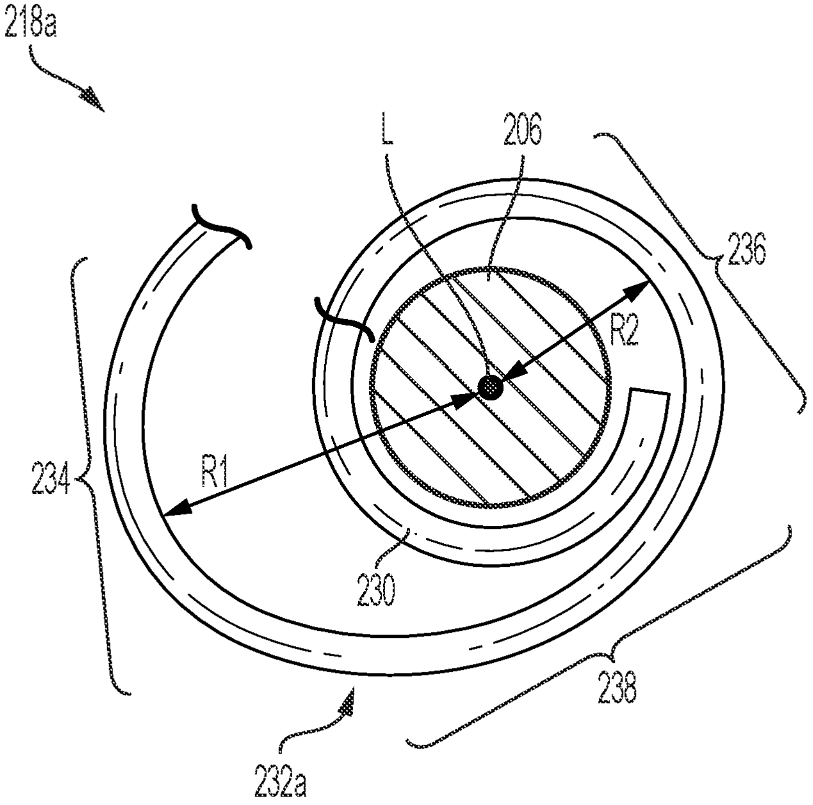
FIG. 2E is an isolated view of one centering element and one winding of the engagement member of FIG. 2D.

In some embodiments, for example as shown in FIGS. 2A-2D, the engagement member 218 comprises a coil formed from a wire or other elongated member wound in a plurality of windings 232. In some embodiments, one or more of the windings 232 corresponds to one or more of the engagement elements 222. For example, the first engagement element 222*a* can comprise a first winding 232*a*, the second engagement element 222*b* can comprise a second winding 232*b*, and/or the third engagement element 222*c* can comprise a third winding 232*c*. FIG. 2E shows an isolated view of one of the centering elements 230 and the first winding 232*a* of the engagement member 218 of FIGS. 2C and 2D (e.g., in an expanded state). FIG. 2E also depicts the core member 206 extending through the engagement member 218 for reference. Only the first winding 232*a* is shown in FIG. 2E for ease of illustration, but any of the windings 232 can have similar features to the first winding 232*a*. As shown in FIG. 2E, the first winding 232*a* can comprise a first length 234 of the wire, a second length 236 of the wire opposed to the first length 234 about a circumference of the first winding 232*a*, and a third length 238 of the wire extending between the first length 234 and the second length 236. According to various embodiments, adjacent windings 232 can be circumferentially offset from one another about the central longitudinal axis L such that all or a portion of a first length 234 of one of the windings 232 does not overlap a first length 234 of an adjacent one of the windings 232.

The second length 236 can be diametrically opposed to the first length 234. In some embodiments, the second length 236 is angularly spaced apart from the first length 234 about the central longitudinal axis L by about 180 degrees. In some embodiments, the second length 236 can be angularly spaced apart from the first length 234 about the central longitudinal axis L by between about 30 degrees to about 330 degrees, between about 60 degrees to about 300 degrees, between about 90 degrees to about 270 degrees, between about 120 degrees to about 240 degrees, or between about 150 degrees to about 210 degrees.

The first length 234 can have a first radius of curvature and the second length 236 can have a second radius of curvature different from the first radius of curvature. In some embodiments, for example as shown in FIG. 2E, the second radius of curvature is less than the first radius of curvature. Each of the first length 234 and the second length 236 can extend from a first end to a second end circumferentially about the central longitudinal axis L of the engagement member 218. An arc length of the first length 234 can be greater than arc length of the second length 236. Additionally or alternatively, a radius of curvature of the first length 234 can be greater than a radius of curvature of the second length 236.

The first length 234 can be radially spaced apart from the central longitudinal axis L by a first radial distance R1 and the second length 236 can be radially spaced apart from the central longitudinal axis L by a second radial distance R2. At least when the engagement member 218 is in the expanded state, the first radial distance R1 can be greater than the second radial distance R2. At least when the engagement member 218 is in the expanded state, the third length 238 can extend radially outwardly from the second length 236 to the first length 234.

Because of the eccentric geometry of the first winding 232*a*, when the expandable member 202 is compressed over the engagement member 218, the first length 234 may initially engage the inner surface of the expandable member 202 while the second length 236 does not initially engage the inner surface of the expandable member 202. Thus, expandable member 202 may (at least initially) apply radially compressive forces to the first length 234 but not the second length 236. Such forces may push the first length 234 closer to the central longitudinal axis L of the engagement member 218, which can cause the second length 236 to move away from the central longitudinal axis L of the engagement member 218. In other words, the first radial distance R1 can decrease while the second radial distance R2 increases. In this manner, the first winding 232*a* can be radially shifted with respect to the central longitudinal axis L when in the compressed state as compared to the expanded state. Moreover, because radial compression is not initially applied to the entire circumference of the first winding 232*a*, the first winding 232*a* is able to shift rather than deform under the compression. By preventing and/or limiting deformation of the first winding 232*a*, the first winding 232*a* can maintain its elasticity and resilience, which can facilitate expansion of the engagement member 218 from the compressed state during delivery of an expandable member.

In some embodiments, for example as shown in FIG. 2E, the centering element 230 (or any other centering element disclosed herein) can comprise a length of wire wound at least partially about the central longitudinal axis L of the engagement member 218. The length of wire comprising the centering element 230 can be continuous, unitary, and/or monolithic with the wire forming the windings 232 of the engagement member 218. The length of wire forming the centering element 230 can have a substantially constant radius of curvature. In some embodiments, the length of wire forming the centering element 230 has a radius of curvature that is similar to or just larger than a radius of curvature of the core member 206. The length of wire forming the centering element 230 may comprise one complete loop (e.g., extending about the central longitudinal axis L by 360 degrees), less than one complete loop (e.g., extending about the central longitudinal axis L by less than 360 degrees), or more than one complete loop (e.g., extending about the central longitudinal axis L by more than 360 degrees).

According to various embodiments, the wire can comprise any metal, polymer, or other biocompatible material. In some embodiments, the material of the wire is based on a desired resilience of the engagement member 218. For example, it may be desirable for the material to be able to withstand a predetermined amount of strain without yielding. In some embodiments, the wire comprises stainless steel, nickel cobalt (e.g., MP35N), Nitinol, alloys thereof, and/or other materials.

FIGS. 3-7 illustrate representative examples of engagement members 318-718 in accordance with embodiments of the present technology. The features of the engagement members 318-718 can be generally similar to the features of the engagement member 118 of FIGS. 1A-1D and/or the features of the engagement member 218 of FIGS. 2A-2E. Accordingly, like numbers (e.g., windings 332 versus windings 232) are used to identify similar or identical components in FIGS. 1A-7, and the discussion of the engagement members 318-718 of FIGS. 3-7 will be largely limited to those features that differ from the engagement members 118, 218 of FIGS. 1A-2E. Additionally, any of the features of the engagement members 318-718 of FIGS. 3-7 can be combined with each other and/or with the features of the engagement members 118, 218 of FIGS. 1A-2E. Any of the systems or coupling assemblies disclosed herein can include any of the engagement members 318-718 of FIGS. 3-7.

Figure 3:
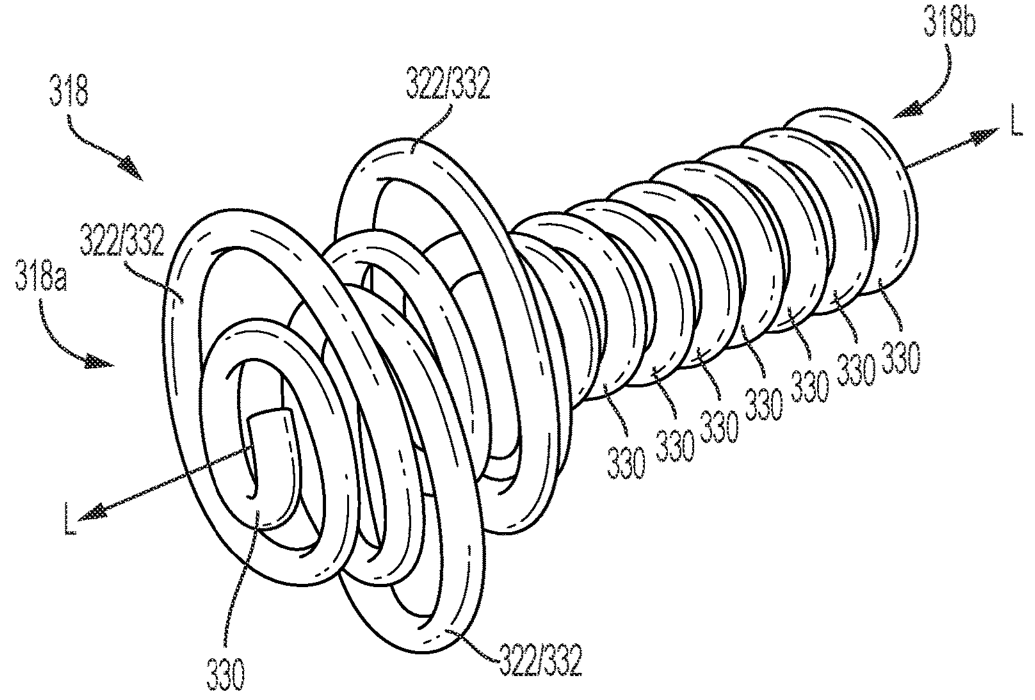
FIGS. 3-7 depict various engagement members in accordance with the present technology.

The engagement member 318 shown in FIG. 3 comprises a first end portion 318*a*, a second end portion 318*b*, and a central longitudinal axis L extending therebetween. Similar to the engagement member 218 of FIGS. 2A-2E, the engagement member 318 of FIG. 3 can comprise a plurality of circumferentially and/or longitudinally offset engagement elements 322. In some embodiments, the engagement member 318 comprises a coil formed from a wire wound about the central longitudinal axis L in a plurality of windings 332, which can correspond to the engagement elements 322. The engagement member 318 can comprise a plurality of centering elements 330. For example, as shown in FIG. 3, the engagement member 318 can comprise one centering element 330 at the first end portion 318*a* of the engagement member 318 and a plurality of centering elements 330 at the second end portion 318*b* of the engagement member 318. The plurality of centering elements 330 at the second end portion 318*b* can comprise a series of contiguous loops. In some embodiments, a diameter of each centering element 330 is slightly larger than an outer diameter of a core member to be received by the centering element(s) 330. The diameters of the centering elements 330 can be similar or can vary along the longitudinal axis L. A pitch of the centering elements 330 can be substantially constant along the longitudinal axis L or may vary.

The plurality of centering elements 330 at the second end portion 318*b* of the engagement member 318 can facilitate centering of the engagement member 318 on a core member, as a greater number of centering elements 330 can better resist movement of the longitudinal axis L of the engagement member 318 away from a core member without substantial deformation of the engagement member 318. Additionally or alternatively, the plurality of centering elements 330 can be fixed to a core member to prevent or limit sliding and/or rotation of at least the second end portion 318*b* of the engagement member 318 relative to the core member. In some embodiments, the plurality of centering elements 330 can serve as a spacer to define a minimum longitudinal distance between the engagement elements/windings 322/332 and an adjacent component of a coupling assembly. In these embodiments and others, a coupling assembly may or may not include a distinct spacer between the engagement member 318 and one or more adjacent components.

Figure 4:
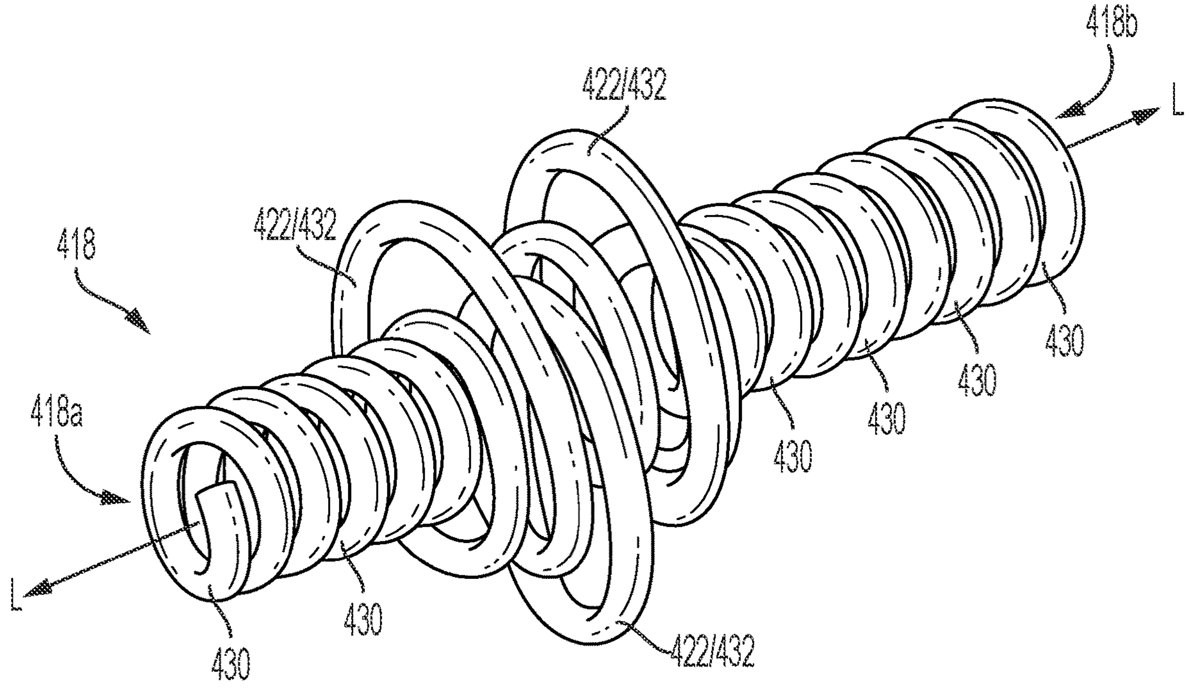

The engagement member 418 shown in FIG. 4 comprises a first end portion 418*a*, a second end portion 418*b*, and a central longitudinal axis L extending therebetween. The engagement member 418 of FIG. 4 can comprise a plurality of circumferentially and/or longitudinally offset engagement elements 422. In some embodiments, the engagement member 418 comprises a coil formed from a wire wound about the central longitudinal axis L in a plurality of windings 432. The engagement member 418 can comprise a plurality of centering elements 430. Similar to the engagement member 318 of FIG. 3, the engagement member 418 of FIG. 4 comprises a plurality of centering elements 430 at the second end portion 418*b* of the engagement member 418 (only a few of which are labeled for ease of illustration). However, instead of a single centering element at the first end portion of the engagement member, engagement member 418 comprises a plurality of centering elements 430 at the first end portion 418*a* (only a few of which are labeled for ease of illustration). Providing multiple centering elements 430 on both sides of the engagement elements/windings 432/432 can further facilitate centering of the engagement member 418 on a core member. Additionally or alternatively, the centering elements 430 positioned on either side of the engagement elements/windings 432/432 can be fixed to a core member to prevent or limit sliding and/or rotation of the engagement member 418 relative to the core member. When the centering elements 430 on both sides of the engagement elements/windings 432/432 are fixed to a core member, elongation of the engagement member 418 under radial compression can be prevented or limited.

Figure 5:
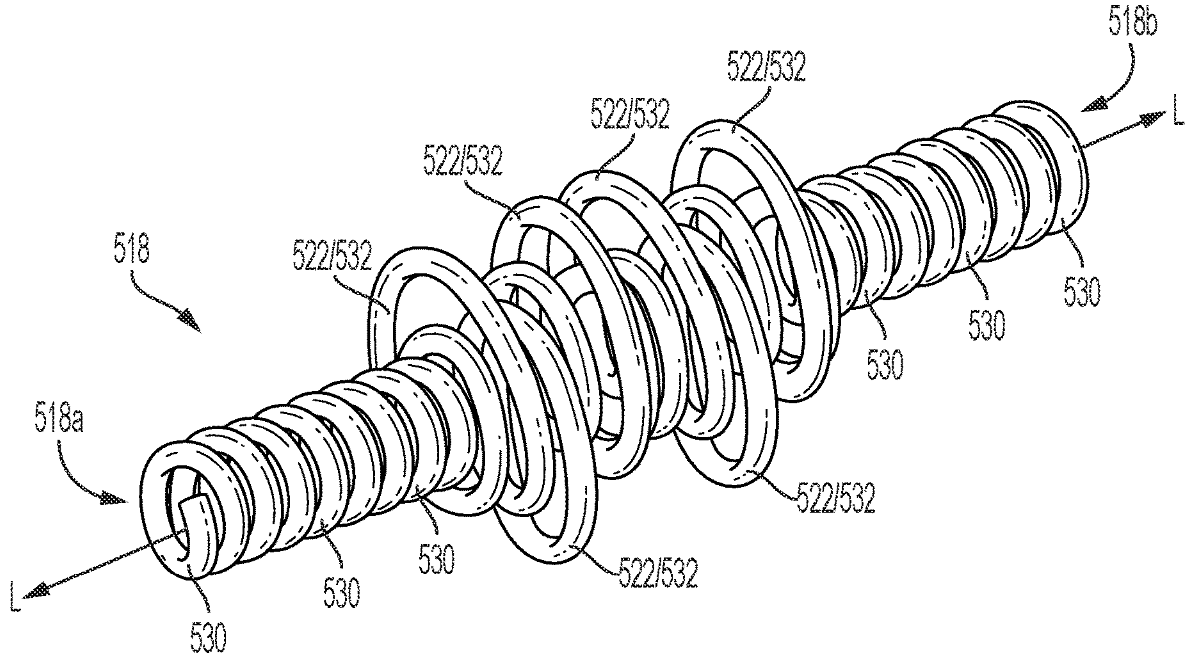

The engagement members 318, 418 of FIGS. 3 and 4 each have three engagement elements/windings 322/332. However, in some embodiments an engagement member can comprise fewer than three or more than three engagement elements and/or windings. For example, the engagement member 518 shown in FIG. 5 comprises a first end portion 518*a*, a second end portion 518*b*, a central longitudinal axis L extending therebetween, and six engagement elements 522. The engagement member 518 can comprise a coil formed from a wire wound about the central longitudinal axis L to form six windings 532 corresponding to the engagement elements 522. By including three more windings 532 than the engagement members 318, 418 of FIGS. 3 and 4, the engagement member 518 may be configured to apply a greater outward force to an overlying expandable member than engagement members 318, 418, which can improve the ability of the engagement member 518 to cause a desired motion of the expandable member. The engagement member 518 can include a plurality of centering elements 530 at the first end portion 518*a* of the engagement member 518 and/or a plurality of centering elements 530 at the second end portion 518*b* of the engagement member 518. Only a few of the centering elements 530 are labeled in FIG. 5 for ease of illustration. As shown in FIG. 5, in some embodiments the engagement member 518 comprises a similar number of centering elements 530 on either side of the engagement elements/windings 522/532.

Figure 6:
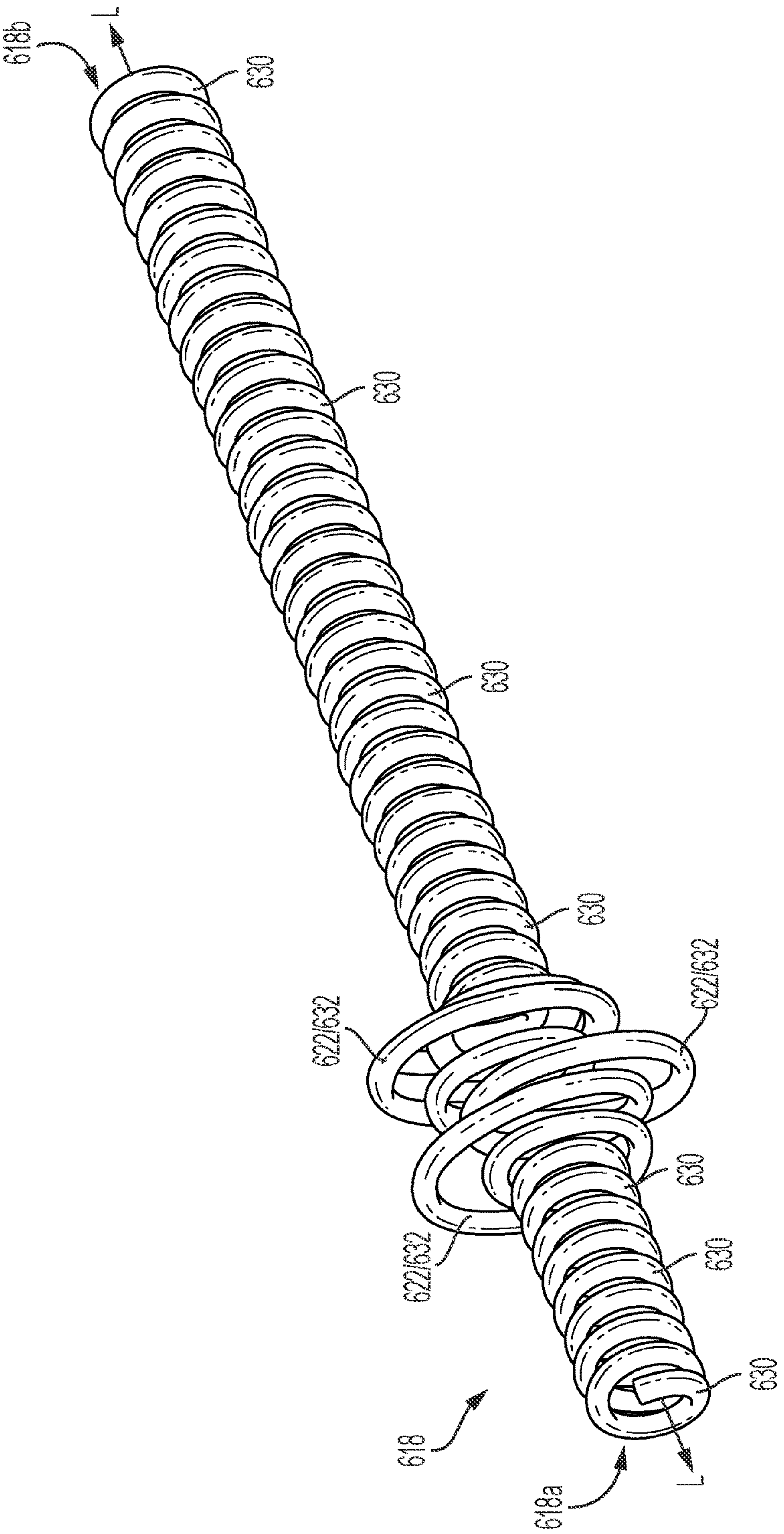
Figure 7:
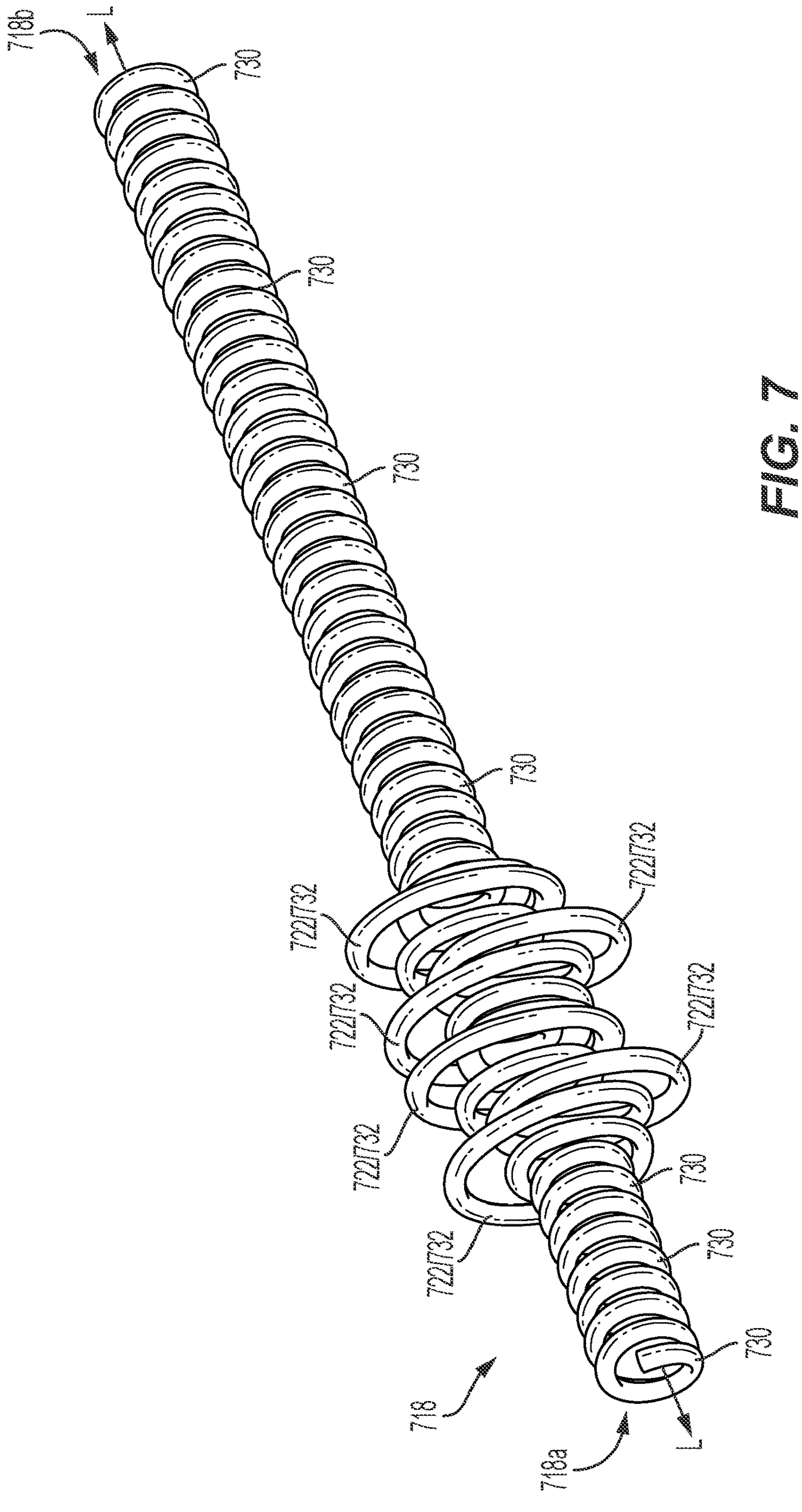

The engagement member 618 shown in FIG. 6 comprises a first end portion 618*a*, a second end portion 618*b*, a central longitudinal axis L extending therebetween, and a plurality of engagement elements 622. The engagement member 618 can comprise a coil formed from a wire wound about the central longitudinal axis L to form a plurality of windings 632 corresponding to the engagement elements 622. The engagement member 618 can comprise a plurality of centering elements 630 (a few of which are labeled in FIG. 6) disposed on either side of the engagement elements/windings 622/632. However, in contrast to the engagement member 518 of FIG. 5, the centering elements 630 engagement member 618 of FIG. 6 can be asymmetrically distributed on either side of the engagement elements/windings 622/632. For example, the engagement member 618 can comprise fewer centering elements 630 at the first end portion 618*a* of the engagement member 618 than at the second end portion 618*b* of the engagement member 618. In some embodiments, the centering elements 630 can serve as a spacer defining a minimum longitudinal distance between the engagement elements/windings 622/632 and adjacent components of a coupling assembly. For example, first end portion 618*a* of the engagement member 618 can be a proximal end portion and the centering elements 630 at the first end portion 618*a* can define a minimum longitudinal distance between the engagement elements/windings 622/632 and an adjacent proximal restraint. Accordingly, it can be advantageous for engagement member 618 to include only a few centering elements 630 at the first end portion 618*a* so that the engagement elements/windings 622/632 will be located close to the proximal restraint and a large length of an expandable member can be released with resheathing remaining possible.

An engagement member of the present technology can include any suitable number or combination of features as disclosed herein. For example, the engagement member 718 shown in FIG. 7 comprises a first end portion 718*a*, a second end portion 718*b*, a central longitudinal axis L extending therebetween, six engagement elements 722 (corresponding to six windings 732), a first plurality of centering elements 730 at the first end portion 718*a* (a few of which are labeled in FIG. 7), and a second, greater plurality of centering elements 7 30 at the second end portion 718*b* (a few of which are labeled in FIG. 7).

Figure 8:
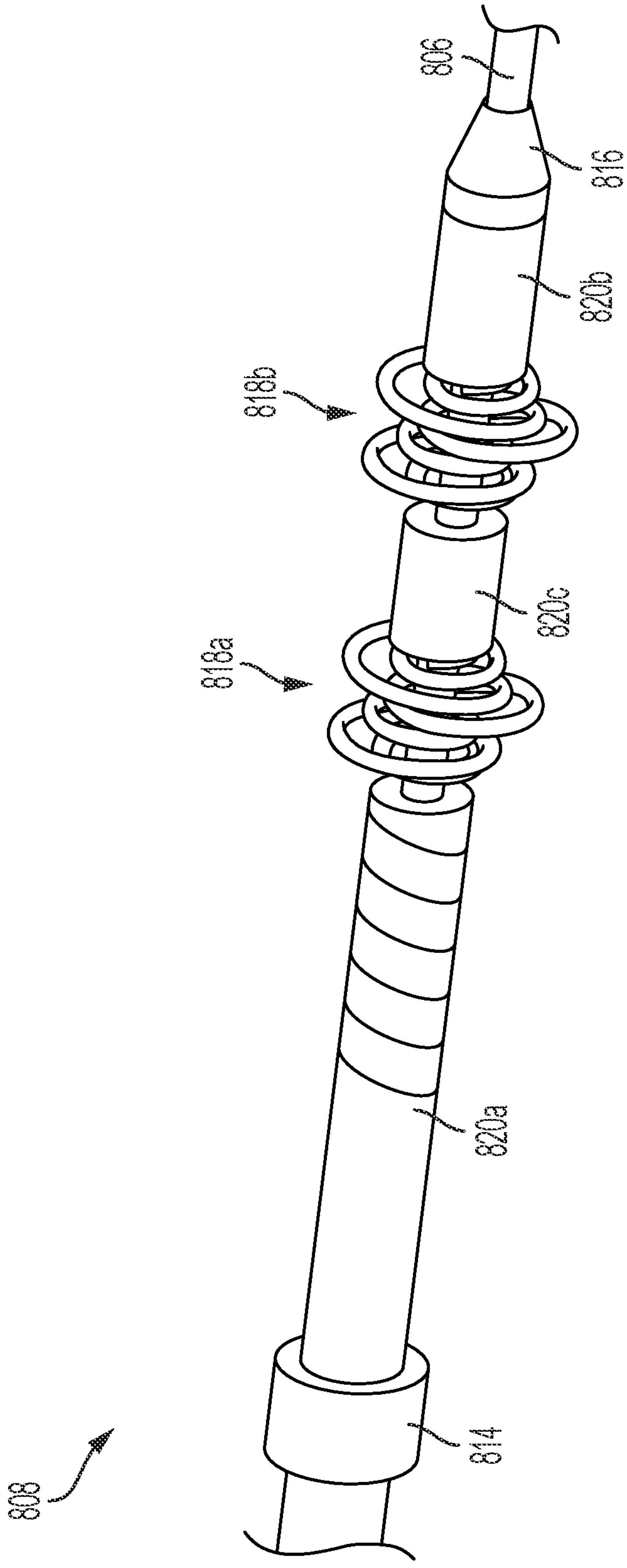
FIG. 8 is a perspective view of a coupling assembly in accordance with the present technology.

Although FIGS. 1A-2E depict coupling assemblies 108, 208 comprising a single engagement member, a coupling assembly of the present technology can comprise multiple engagement members. For example, FIG. 8 depicts a coupling assembly 808 carried by a core member 806 and including a proximal restraint 814, a distal restraint 816, a first engagement member 818*a*, and a second engagement member 818*b*. In some embodiments, the first engagement member 818*a* can be longitudinally separated from the proximal restraint 814 by a first spacer 820*a* and/or the second engagement member 818*b* can be separated from the distal restraint 816 by a second spacer 820*b*. Additionally or alternatively, the first engagement member 818*a* can be separated from the second engagement member 818*b* by a third spacer 820*c*. In some embodiments, coupling assembly 808 does not include the first spacer 820*a*, the second spacer 820*b*, and/or the third spacer 820*c*. The features of the coupling assembly 808 can be generally similar to the features of the coupling assemblies 108, 208 of FIGS. 1A-2E. Accordingly, like numbers (e.g., engagement members 818*a*, 818*b* versus engagement member 118) are used to identify similar or identical components in FIGS. 1A-2E. Additionally, any of the features of the coupling assembly 808 can be combined with each other and/or with the features of the coupling assemblies 108, 208 of FIGS. 1A-2E.

CONCLUSION

Although many of the embodiments are described above with respect to systems, devices, and methods for delivery of an expandable member such as a medical device to a treatment site within a blood vessel, the technology is applicable to other applications and/or other approaches. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 1-8.

As used herein, the terms "distal" and "proximal" define a position or direction with respect to a clinician or a clinician's control device (e.g., a handle of a delivery catheter). For example, the terms, "distal" and "distally" refer to a position distant from or in a direction away from a clinician or a clinician's control device along the length of device. In a related example, the terms "proximal" and "proximally" refer to a position near or in a direction toward a clinician or a clinician's control device along the length of device.

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

As used herein, the terms "generally," "substantially," "about," and similar terms are used as terms of approximation and not as terms of degree, and are intended to account for the inherent variations in measured or calculated values that would be recognized by those of ordinary skill in the art.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A device for facilitating delivery of an expandable member through an elongated shaft to a treatment site within a blood vessel, the device comprising:

a first end, a second end, and a central longitudinal axis extending therebetween; and a first engagement element and a second engagement element, wherein the first engagement element is offset from the second engagement element along the central longitudinal axis, wherein each of the first engagement element and the second engagement element are eccentrically shaped and defined by a perimeter comprising a first region and a second region, wherein the device is configured to be transitioned between a radially expanded state and a radially compressed state, wherein each of the first regions is closer to the central longitudinal axis in the radially compressed state than in the radially expanded state and each of the second regions is farther from the central longitudinal axis in the radially compressed state than in the radially expanded state, wherein the device is configured to be positioned in the elongated shaft in the radially compressed state with the expandable member positioned between the device and an inner surface of the elongated shaft, and wherein the device comprises a resilient material such that, when the device is positioned in a lumen of the elongated shaft in the radially compressed state, the first and second engagement elements exert an outward force against the expandable member and the inner surface of the lumen of the elongated shaft and, when the device is positioned outside of the lumen of the elongated shaft, the first regions move away from the central longitudinal axis and the second regions move toward the central longitudinal axis.

2. The device of claim 1 wherein each of the first regions and each of the second regions extends circumferentially about the central longitudinal axis.

3. The device of claim 1, wherein with the device in the radially expanded state, the first and second engagement elements are circumferentially offset from one another about the central longitudinal axis such that all or a portion of the first region of the first engagement element does not circumferentially overlap the first region of the second engagement element.

4. The device of claim 1, wherein, with the device in the radially expanded state, the first region of the first engagement element is diametrically opposed to the second region of the first engagement element, and the first region of the second engagement element is diametrically opposed to the second region of the second engagement element.

5. The device of claim 1, wherein, with the device in the radially expanded state, an arc length of each of the first regions is greater than an arc length of each of the second regions.

6. The device of claim 1, wherein, with the device in the radially expanded state, a radius of curvature of each of the first regions is greater than a radius of curvature of each of the second regions.

7. A device for facilitating delivery of an expandable member through an elongated shaft to a treatment site within a blood vessel, the device comprising:

a coil comprising a first end portion, a second end portion, and a central longitudinal axis extending therebetween, the coil comprising a plurality of windings including a first winding and a second winding, wherein the coil is transitionable between a radially expanded state and a radially compressed state, and wherein, with the coil in the radially expanded state:

a first length of the first winding defines a first radius of curvature and a second length of the first winding defines a second radius of curvature less than the first radius of curvature, wherein the first length and the second length of the first winding are diametrically opposed and the first length is positioned farther from the central longitudinal axis than the second length, and a first length of the second winding defines a third radius of curvature and a second length of the second winding defines a fourth radius of curvature less than the third radius of curvature, wherein the first length and the second length of the second winding are diametrically opposed and the first length of the second winding is positioned farther from the central longitudinal axis than the second length of the second winding, and wherein the coil is configured to be positioned in the elongated shaft in the radially compressed state with the expandable member positioned between the coil and an inner surface of the elongated shaft, and wherein the coil comprises a resilient material such that, with the coil positioned in a lumen of the elongated shaft in the radially compressed state, the first lengths of the first winding and the second winding exert an outward force against the expandable member and the inner surface of the elongated shaft and, with the device transitioning from being positioned within the lumen of the elongated shaft to not being positioned within the lumen of the elongated shaft, the first lengths move away from the central longitudinal axis.

8. The device of claim 7, wherein with the coil in the radially expanded state, the first winding and the second winding are circumferentially offset from one another about the central longitudinal axis such that all or a portion of the first length of the first winding does not circumferentially overlap the first length of the second winding.

9. The device of claim 7, wherein, with the coil in the radially expanded state, an arc length of each of the first lengths is greater than an arc length of each of the second lengths.

10. The device of claim 7, wherein an outer diameter of the coil in the radially compressed state is at least 20% smaller than an outer diameter of the coil in the radially expanded state.

11. The device of claim 7, further comprising one or more centering windings configured to limit radial movement of the coil relative to a core member extending through the coil, wherein each of the one or more centering windings is located proximally or distally of the first and second windings.

12. The device of claim 7, wherein the coil comprises a stainless steel or a nickel cobalt alloy.

13. A system for delivering an expandable member through an elongated shaft to a treatment site within a blood vessel, the system comprising:

a core member configured to be slidably positioned within the elongated shaft, the core member comprising a proximal portion and a distal portion, wherein the distal portion is configured to be intravascularly positioned within a blood vessel; and a distal member carried by the distal portion of the core member, wherein the distal member comprises:

a first end portion, a second end portion, and a central longitudinal axis extending therebetween; and a first engagement element and a second engagement element, wherein the first engagement element and the second engagement element are each eccentrically shaped and defined by a perimeter comprising a first region and a second region, wherein the distal member is transitionable between a radially expanded state and a radially compressed state, wherein each of the first regions is closer to the central longitudinal axis in the radially compressed state than in the radially expanded state and each of the second regions is farther from the central longitudinal axis in the radially compressed state than in the radially expanded state, wherein the distal member is configured to be positioned in the elongated shaft in the radially compressed state with the expandable member positioned between the distal member and an inner surface of the elongated shaft, and wherein the distal member comprises a resilient material such that, with the distal member positioned in a lumen of the elongated shaft in the radially compressed state, the first engagement element and the second engagement element exert an outward force against the expandable member and the inner surface of the elongated shaft, and, with the distal member transitioning from being positioned within the lumen of the elongated shaft to not being positioned within the lumen of the elongated shaft, the first regions move away from the central longitudinal axis.

14. The system of claim 13, wherein the first end portion of the distal member is fixed to the core member and the second end portion of the distal member can translate and/or rotate with respect to the core member.

15. The system of claim 13, wherein the first end portion and the second end portion of the distal member are fixed relative to the core member.

16. The system of claim 13, wherein the first end portion and the second end portion of the distal member are translatable and/or rotatable relative to the core member.

17. The system of claim 13, wherein a length of the distal member in the radially compressed state is greater than a length of the distal member in the radially expanded state.

18. The system of claim 13, wherein the distal member comprises a coil.

19. The system of claim 13, further comprising a proximal restraint positioned proximally of the distal member and configured to apply distally directed force to the expandable member and a distal restraint positioned distally of the distal member and configured to limit distal movement of the distal member relative to the core member.

20. The system of claim 13, wherein the expandable member is braided.

* * * * *